US009259240B2

(12) United States Patent
Malkowski et al.

(10) Patent No.: US 9,259,240 B2
(45) Date of Patent: Feb. 16, 2016

(54) ARTICULATING SURGICAL ACCESS SYSTEM FOR LAPAROSCOPIC SURGERY

(75) Inventors: Jaroslaw T. Malkowski, Trumbull, CT (US); Eric Taylor, East Hampton, CT (US); Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 848 days.

(21) Appl. No.: 13/412,079

(22) Filed: Mar. 5, 2012

(65) Prior Publication Data

US 2012/0253131 A1 Oct. 4, 2012

Related U.S. Application Data

(60) Provisional application No. 61/469,001, filed on Mar. 29, 2011.

(51) Int. Cl.
*A61B 1/32* (2006.01)
*A61B 17/34* (2006.01)
(Continued)

(52) U.S. Cl.
CPC ......... *A61B 17/3421* (2013.01); *A61B 17/3423* (2013.01); *A61B 19/2203* (2013.01); *A61B 17/3431* (2013.01); *A61B 2017/00314* (2013.01); *A61B 2017/00327* (2013.01);
(Continued)

(58) Field of Classification Search
CPC ............... A61B 17/29; A61B 17/3421; A61B 17/00234; A61B 17/0218; A61B 17/0469; A61B 17/3423; A61B 17/00323; A61B 17/2908; A61B 2017/2906; A61B 2017/3445; A61B 2017/003; A61B 2017/2927; A61B 2017/3447; A61B 2017/347; A61B 2017/0046; A61B 2017/2905
See application file for complete search history.

(56) References Cited

U.S. PATENT DOCUMENTS 5,312,391 A * 5/1994 Wilk ................................. 606/1
5,312,417 A   5/1994 Wilk
(Continued)

FOREIGN PATENT DOCUMENTS

CA   2702419   11/2010
EP   1312318   5/2003
(Continued)

OTHER PUBLICATIONS

European Search Report 11194126.6-2310 dated Feb. 5, 2012.
(Continued)

*Primary Examiner* — Mary Hoffman

(57) ABSTRACT

A surgical system includes one or more arms defining a passageway therethrough. The arm includes a proximal portion configured for positioning externally of a patient's body and a distal portion configured for positioning within an internal body cavity. The distal portion includes first and second articulatable segments spaced apart from one another and capable of independent articulation between a substantially straight configuration and an articulated configuration. A first articulation assembly is coupled to the proximal portion of the one arm and is transitionable between a first state and a second state for articulating the first articulatable segment between the substantially straight configuration and the articulated configuration. A second articulation assembly is coupled to the proximal portion of the arm and is configured to move between a plurality of positions for articulating the second articulatable segment between the substantially straight configuration and the articulated configuration.

15 Claims, 22 Drawing Sheets

(51) Int. Cl.
*A61B 19/00* (2006.01)
*A61B 17/00* (2006.01)
*A61B 17/29* (2006.01)

(52) U.S. Cl.
CPC  *A61B 2017/2906* (2013.01); *A61B 2017/2908* (2013.01); *A61B 2017/3445* (2013.01); *A61B 2017/3447* (2013.01); *A61B 2019/2215* (2013.01); *A61B 2019/2238* (2013.01)

(56) References Cited

U.S. PATENT DOCUMENTS

| | | | |
|---|---|---|---|
| 5,318,013 A * | 6/1994 | Wilk | 600/222 |
| 5,391,156 A | 2/1995 | Hildwein et al. | |
| 5,395,367 A * | 3/1995 | Wilk | 606/1 |
| 5,441,483 A | 8/1995 | Avitall | |
| 5,511,564 A | 4/1996 | Wilk | |
| 5,520,678 A | 5/1996 | Heckele et al. | |
| 5,904,703 A | 5/1999 | Gilson | |
| 5,906,577 A | 5/1999 | Beane et al. | |
| 6,048,309 A | 4/2000 | Flom et al. | |
| 6,562,022 B2 | 5/2003 | Hoste et al. | |
| 6,929,637 B2 | 8/2005 | Gonzalez et al. | |
| 7,011,645 B2 | 3/2006 | McGuckin, Jr. et al. | |
| 7,052,454 B2 | 5/2006 | Taylor | |
| 7,300,399 B2 | 11/2007 | Bonadio et al. | |
| 7,473,221 B2 | 1/2009 | Ewers et al. | |
| 7,559,893 B2 | 7/2009 | Bonadio et al. | |
| 7,682,319 B2 | 3/2010 | Martin et al. | |
| 7,758,500 B2 | 7/2010 | Boyd et al. | |
| 7,766,824 B2 | 8/2010 | Jensen et al. | |
| 7,787,963 B2 | 8/2010 | Geistert et al. | |
| 7,798,998 B2 | 9/2010 | Thompson et al. | |
| 7,811,277 B2 | 10/2010 | Boulais | |
| 8,157,786 B2 | 4/2012 | Miller et al. | |
| 8,187,177 B2 | 5/2012 | Kahle et al. | |
| 8,187,178 B2 | 5/2012 | Bonadio et al. | |
| 2003/0014076 A1 | 1/2003 | Mollenauer et al. | |
| 2003/0093104 A1 | 5/2003 | Bonner et al. | |
| 2003/0149422 A1 | 8/2003 | Muller | |
| 2004/0054322 A1 | 3/2004 | Vargas | |
| 2004/0138525 A1 * | 7/2004 | Saadat et al. | 600/104 |
| 2004/0249367 A1 * | 12/2004 | Saadat et al. | 606/1 |
| 2005/0222495 A1 * | 10/2005 | Okada et al. | 600/114 |
| 2005/0228224 A1 * | 10/2005 | Okada et al. | 600/104 |
| 2005/0251091 A1 * | 11/2005 | Saadat et al. | 604/96.01 |
| 2006/0149306 A1 | 7/2006 | Hart et al. | |
| 2006/0161049 A1 | 7/2006 | Beane et al. | |
| 2006/0247500 A1 | 11/2006 | Voegele et al. | |
| 2006/0247516 A1 | 11/2006 | Hess et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2008/0045803 A1 * | 2/2008 | Williams et al. | 600/204 |
| 2008/0051631 A1 | 2/2008 | Dejima et al. | |
| 2008/0097332 A1 | 4/2008 | Greenhalgh et al. | |
| 2010/0004591 A1 | 1/2010 | Barenboym et al. | |
| 2010/0004633 A1 | 1/2010 | Rothe et al. | |
| 2010/0063452 A1 | 3/2010 | Edelman et al. | |
| 2010/0121147 A1 | 5/2010 | Oskin et al. | |
| 2010/0188869 A1 | 7/2010 | Fredette et al. | |
| 2010/0280326 A1 | 11/2010 | Hess et al. | |
| 2010/0298646 A1 | 11/2010 | Stellon et al. | |
| 2011/0054260 A1 | 3/2011 | Albrecht et al. | |
| 2011/0184231 A1 * | 7/2011 | Page et al. | 600/104 |
| 2011/0230723 A1 * | 9/2011 | Castro et al. | 600/205 |
| 2012/0253131 A1 * | 10/2012 | Malkowski et al. | 600/201 |

FOREIGN PATENT DOCUMENTS

| | | |
|---|---|---|
| EP | 2226025 | 9/2010 |
| EP | 2229900 | 9/2010 |
| EP | 2253283 | 11/2010 |
| WO | WO2004/054456 | 7/2004 |
| WO | WO2010/141409 | 12/2010 |

OTHER PUBLICATIONS

European Search Report 11250792.6-2310 dated Feb. 24, 2012.

* cited by examiner

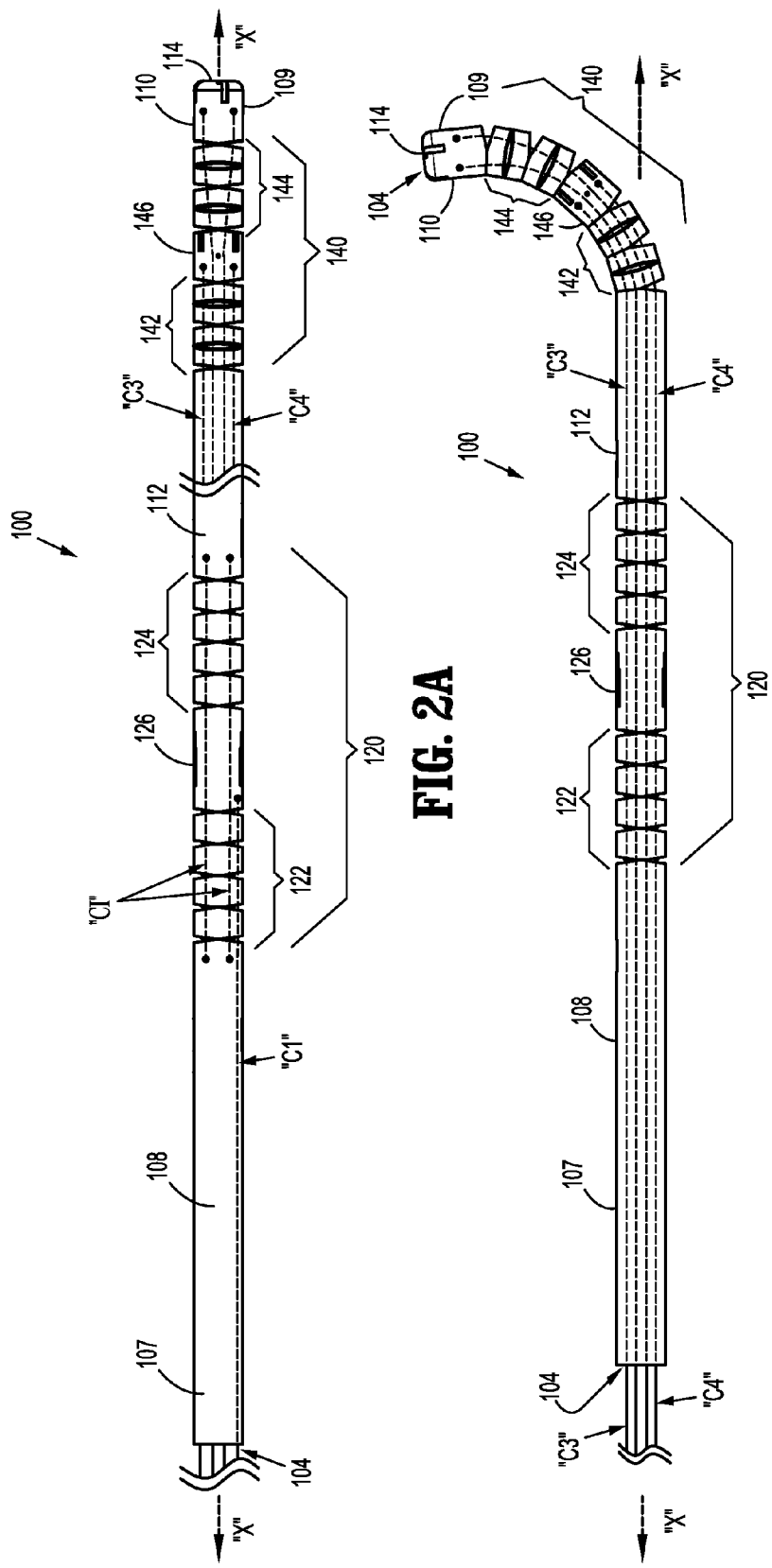

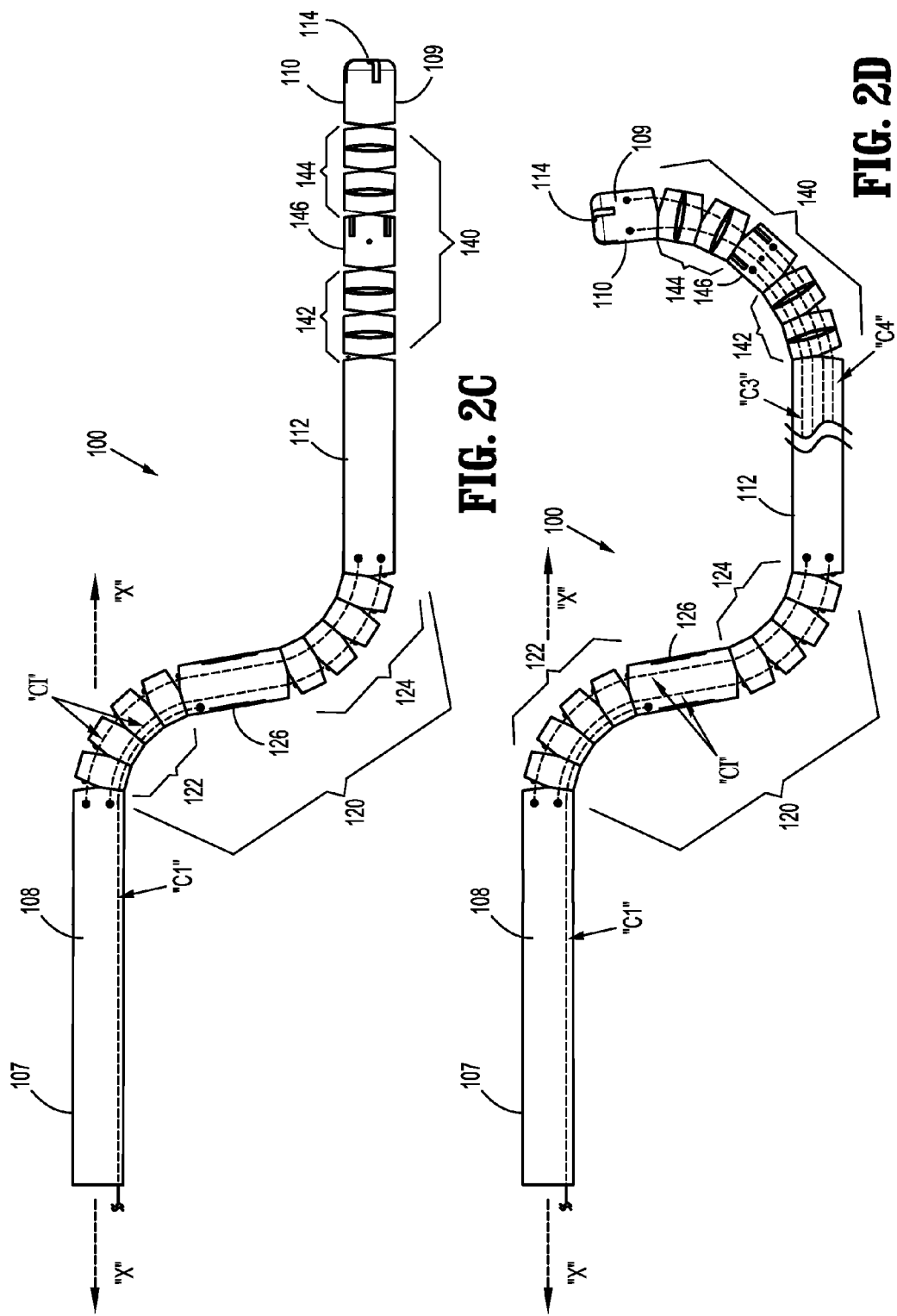

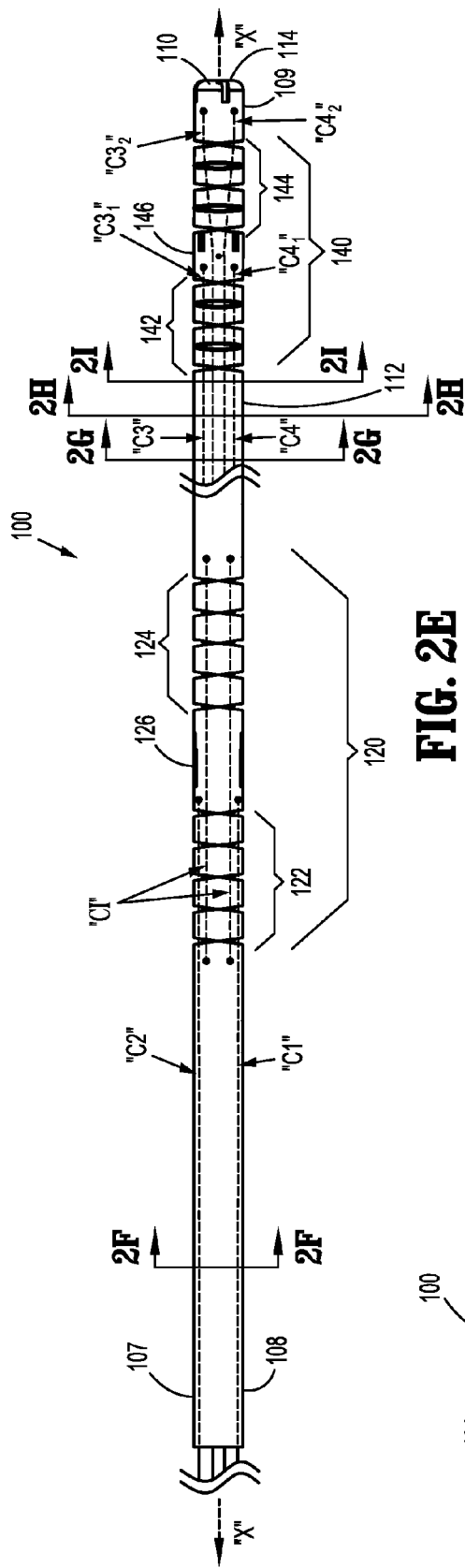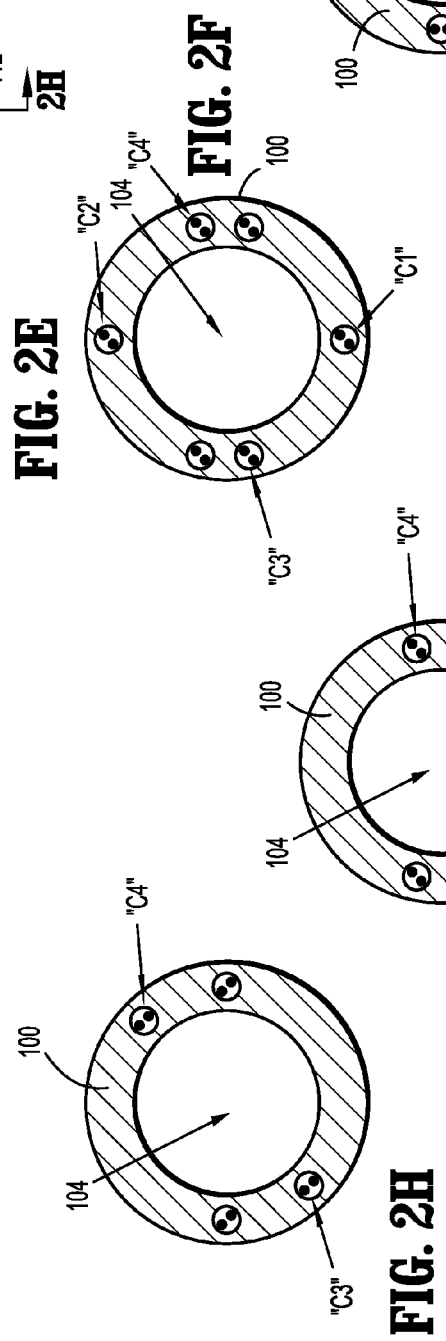

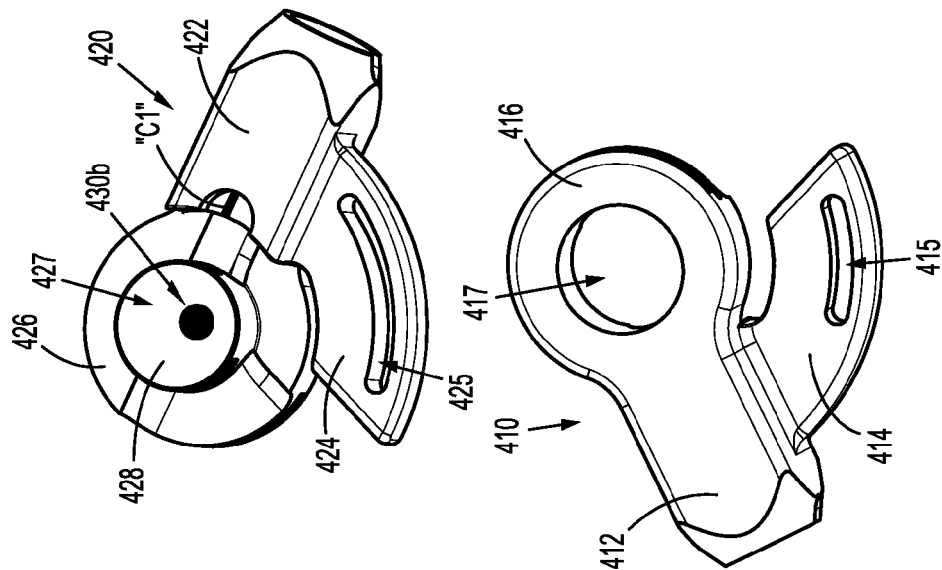
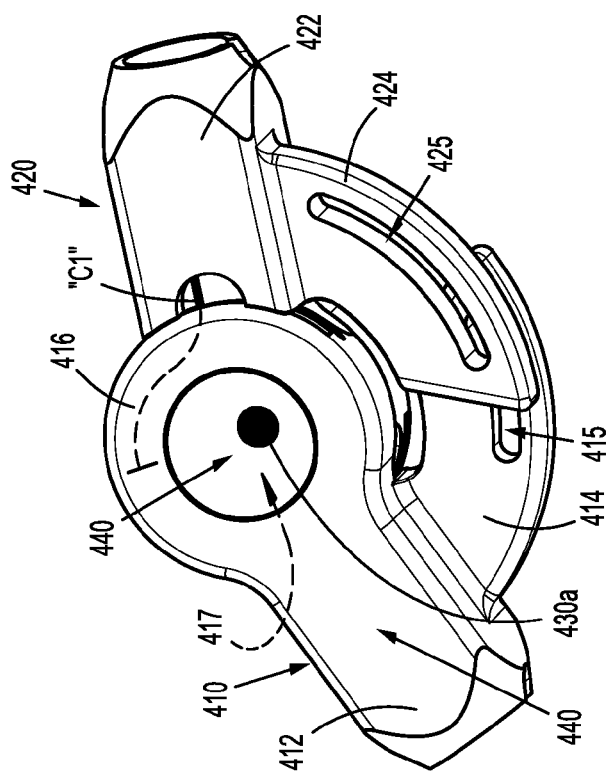
FIG. 12C
FIG. 12B

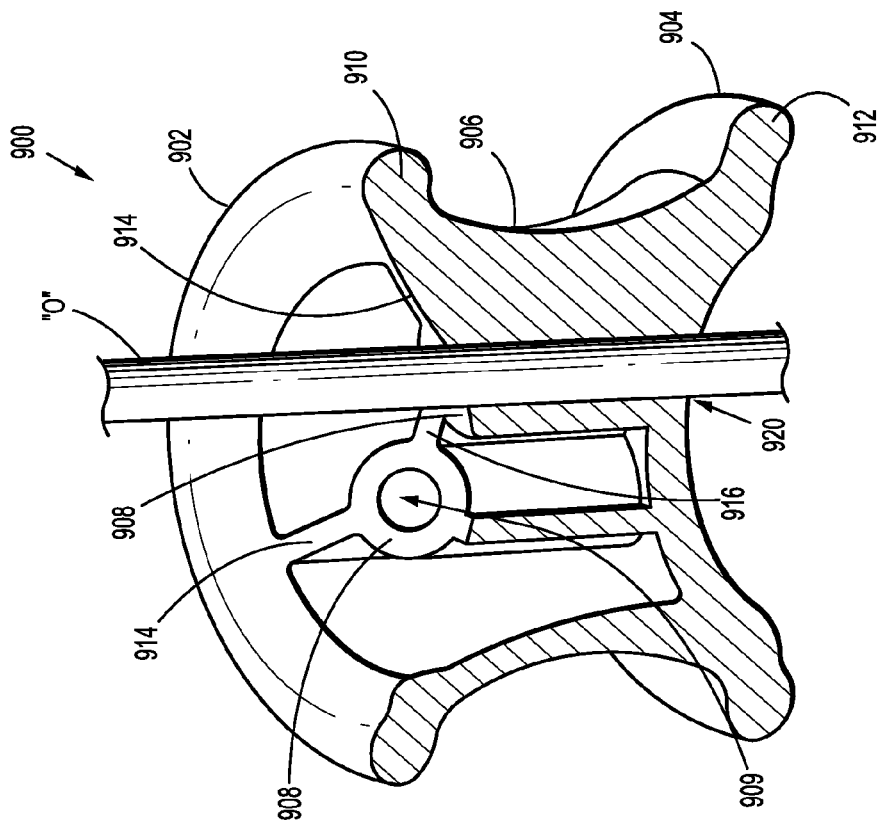
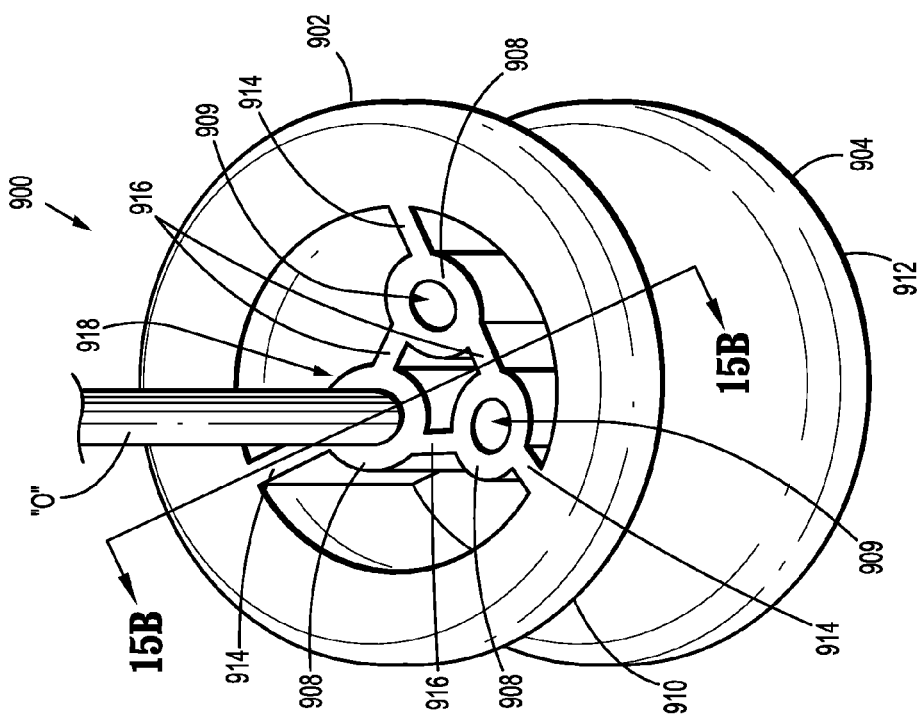

ARTICULATING SURGICAL ACCESS SYSTEM FOR LAPAROSCOPIC SURGERY

CROSS-REFERENCE TO RELATED APPLICATIONS

This application claims the benefit of and priority to U.S. Provisional Patent Application No. 61/469,001 filed on Mar. 29, 2011, the entire disclosure of which is incorporated by reference herein.

BACKGROUND

1. Technical Field

The present disclosure relates to a surgical access device, and more particularly, to an articulating surgical access system for use in laparoscopic surgical procedures.

2. Background of Related Art

In laparoscopic and endoscopic surgical procedures, a small incision or puncture is made in a patient's body, e.g., in the abdomen, to provide an entry point for a surgical access device which is inserted into the incision and facilitates the insertion of instruments used in performing surgical procedures within an internal surgical site. Laparoscopic surgical procedures are advantageous in that, as compared to traditional open surgical procedures, both trauma to the patient and recovery time are reduced due to the relatively small incisions formed through the patient's body. However, since these access incisions are small, only elongated, small diametered instrumentation may be used to access the internal body cavities and organs.

During such procedures, surgical objects such as surgical access devices, e.g., trocar and cannula assemblies, are inserted into the patient's body through the incision in tissue. In general, prior to the introduction of the surgical object into the patient's body, insufflation gases are used to enlarge the area surrounding the target surgical site to create a larger, more accessible work area. The surgeon is then able to perform the procedure within the abdominal cavity by manipulating the instruments that have been extended through the access devices. The manipulation of such instruments within the internal body is similarly limited by both spatial constraints and the need to maintain the body cavity in an insufflated state.

SUMMARY

In accordance with one embodiment of the present disclosure, a surgical system is provided. The surgical system includes one or more arms defining a longitudinal passageway extending therethrough that is configured to receive a surgical instrument therein. The arm(s) includes a proximal portion configured for positioning externally of a patient's body and a distal portion configured for positioning within an internal body cavity. The distal portion includes first and second articulatable segments spaced-apart from one another and capable of independent articulation between a substantially straight configuration and an articulated configuration. A first articulation assembly is coupled to the proximal portion of the arm and is transitionable between a first state and a second state for articulating the first articulatable segment between the substantially straight configuration and the articulated configuration. A second articulation assembly (different from the first articulation assembly) is coupled to the proximal portion of the arm and is configured to move through a plurality of positions for articulating the second articulatable segment between the substantially straight configuration and the articulated configuration.

In one embodiment, one or more sets of articulation cables extend from each of the first and second articulatable segments to the first and second articulation assemblies, respectively. The articulation cables are selectively tensionable for articulating the respective articulatable segment from which they extend.

In another embodiment, the first articulation assembly includes a lever and a base. The lever is movable relative to the base between a spaced-apart position and an approximated position for articulating the first articulatable segment between the substantially straight configuration and the articulated configuration. A locking assembly may also be provided to fix the lever in position relative to the base, thereby fixing the position of the first articulatable segment. Further, the locking assembly may be automatically engaged to lock the lever in position when the lever is moved to the approximated position such that the first articulatable segment is automatically locked in the articulated position.

In still another embodiment, the first articulation assembly includes first and second components pivotable relative to one another between a substantially aligned position and a substantially transverse position for articulating the first articulatable segment between the substantially straight configuration and the articulated configuration. Further, a locking assembly may be provided. The locking assembly is configured to fix the first and second components in position relative to one another upon pivotable movement of the first and second components to one or more pre-determined positions relative to one another. More specifically, the locking assembly may include a slide block selectively translatable to release the first and second components from fixed position relative to one another.

In yet another embodiment, an access portal is provided. The access portal is configured for positioning within an incision in tissue and to receive the arm therethrough such that the distal portion of the arm is positioned within the internal body cavity.

In still yet another embodiment, the second articulation assembly includes a base defining a cavity and a rotatable member movably disposed in the cavity of the base. The rotatable member is movable relative to the base to articulate the second articulatable segment between the substantially straight and articulated configurations. The rotatable member is further transitionable between an unlocked state, wherein the rotatable member is movable within the cavity of the base relative to the base, and a locked state, wherein an orientation of the rotatable member is fixed relative to the base.

In another embodiment, the rotatable member includes a port extending therethrough in communication with the longitudinal passageway of the arm. The port is configured to receive the surgical instrument therein. In such an embodiment, movement of the surgical instrument disposed within the port of the rotatable member relative to the base articulates the second articulatable segment between the substantially straight and articulated configurations.

BRIEF DESCRIPTION OF THE DRAWINGS

Various embodiments of the present disclosure are described hereinbelow with reference to the drawings, wherein:

FIG. 2A is a side view of a cannula arm configured for use with the surgical access system of FIG. 1 disposed in a first configuration;

FIG. 2B is a side view of the cannula arm of FIG. 2A disposed in a second configuration;

FIG. 2C is a side view of the cannula arm of FIG. 2A disposed in a third configuration;

FIG. 2D is a side view of the cannula arm of FIG. 2A disposed in a fourth configuration;

FIG. 2E is a side view of another embodiment of a cannula arm configured for use with the surgical access system of FIG. 1;

FIG. 2F is a transverse, cross-sectional view of the cannula arm of FIG. 2E taken across section line 2F-2F;

FIG. 2G is a transverse, cross-sectional view of the cannula arm of FIG. 2E taken across section line 2G-2G;

FIG. 2H is a transverse, cross-sectional view of the cannula arm of FIG. 2E taken across section line 2H-2H;

FIG. 2I is a transverse, cross-sectional view of the cannula arm of FIG. 2E taken across section line 2I-2I;

FIG. 12B is an enlarged, perspective view of the articulation assembly of FIG. 12B;

FIG. 12C is an enlarged, exploded view of the articulation assembly of FIG. 12A;

FIG. 15A is top, perspective view of yet another embodiment of a surgical access port configured for use with surgical access system of FIG. 1;

FIG. 15B is longitudinal, cross-sectional view of the access port of FIG. 15A.

DETAILED DESCRIPTION OF EMBODIMENTS

Figure 1:
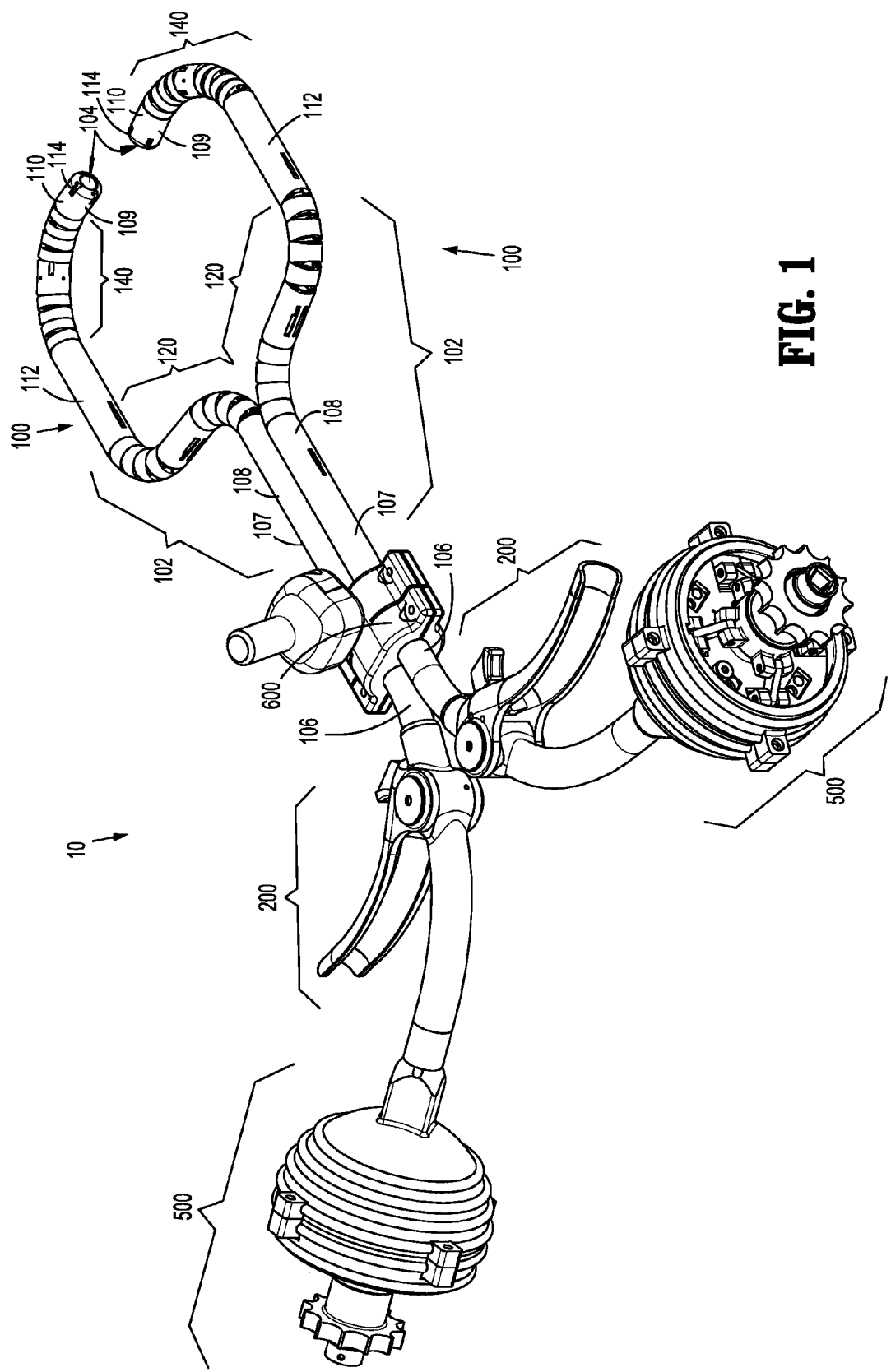
FIG. 1 is a top, perspective view of a surgical access system provided in accordance with one embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user, while the term "proximal" will refer to that portion of the instrument, apparatus, device or component thereof which is closer to the user. In the following description, well-known functions or constructions are not described in detail to avoid obscuring the present disclosure in unnecessary detail.

Turning to FIG. 1, an articulatable surgical access system is shown generally identified by reference numeral 10. Surgical access system 10 is configured for insertion through an access port, e.g., access port 700 (FIGS. 13A-13F), positioned within an incision in tissue or a naturally occurring orifice (e.g., anus or vagina) to facilitate performing one or more minimally-invasive or laparoscopic surgical tasks within an internal surgical site. Surgical access system 10 generally includes a pair of articulatable cannula arms 100, each of which includes a first articulatable segment 120 and a second articulatable segment 140, both of which are disposed toward the distal portions 102 of cannula arms 100. Each cannula arm 100 defines a longitudinal passageway 104 extending therethrough that is configured to receive a surgical instrument "I" (FIGS. 8 and 16) therein. Cannula arms 100 each further include a proximal articulation assembly, e.g., a lever assembly 200, coupled thereto and configured for controlling articulation of one of the articulatable segments, e.g., first articulatable segment 120, and a gimbal assembly 500 mounted to the proximal end 106 thereof for controlling articulation of the other articulatable segment, e.g., second articulatable segment 140, as will be described in greater detail below. Cannula arms 100 are independently articulatable relative to one another and may be joined by a retaining clip 600, or other suitable structure.

Each of the cannula arms 100, gimbal assemblies 500, and the components thereof are substantially similar to one another and, thus, reference herein will be made to only one of the cannula arms 100, gimbal assemblies 500, and corresponding components thereof to avoid unnecessary repetition. However, it is also envisioned that the various embodiments of cannula arms 100 and the components thereof described herein may be interchanged with one another to define different configurations and/or to provide a surgical access system 10 having two different cannula arms 100, depending on the surgical purpose to be achieved.

Turning now to FIGS. 2A-2D, the various articulated configurations of cannula arm 100 will be described. Although four (4) particular configurations of cannula arm 100 are shown in FIGS. 2A-2D, it is envisioned that various other configurations may be provided, e.g., cannula arm 100 may be configured to articulate off of longitudinal axis "X-X" in any direction (i.e., 360 degree articulation). Further, as will be described below, the first and second articulatable segments 120, 140, respectively, are controllable, e.g., movable between the four (4) configurations, via manipulation of proximal articulation assembly 200 and gimbal assembly 500, respectively. In particular, cannula arm 100 includes a plurality of sets of tension wires, or cables "C1" and "C3"-"C4" extending proximally from the first and second articulatable segments 120, 140, respectively, to the respective articulation control assemblies thereof, e.g., proximal articulation assembly 200 and gimbal assembly 500, for controlling the articulation of cannula arm 100 between the various configurations. While reference is made herein to cable sets "C1" and "C3"-"C4" for articulating articulatable segments 120 and 140, it is envisioned that different numbers and/or configurations of cable sets may be provided to achieve different degrees or configurations of articulation of cannula arm 100. For example, four sets of cables may be used in conjunction with each of the articulatable segments 120, 140, to facilitate 360 degree articulation of cannula arm 100. However, to facilitate understanding, only cable sets "C1" and "C3"-"C4" will be described with reference to FIGS. 2A-2D and with respect to the articulation of cannula arm 100 through four different configurations, keeping in mind that the articulation of cannula arm 100 need not be limited to certain degrees of articulation or specific configurations, i.e., cannula arm 100 may be capable of 360 degree articulation relative to longitudinal axis "X-X" and may be articulated to various configurations between the unarticulated and fully articulated configurations thereof. The specific components and features of each of the embodiments of the articulation control assemblies for use with cannula arm 100 will be described in greater detail hereinbelow with reference those various embodiments.

Continuing with reference to FIGS. 2A-2D, and as mentioned above, the distal portion 102 of cannula arm 100 includes first and second articulatable segments 120, 140, respectively that are independently articulatable relative to one another. More specifically, distal portion 102 of cannula arm 100 includes a substantially rigid tubular member 108 disposed at a proximal end 107 thereof and a distal cap 110 disposed at a distal end 109 thereof. First articulatable segment 120 is positioned distally of and adjacent to tubular member 108, while second articulatable segment 140 is positioned proximally of and adjacent to distal cap 110, with a substantially rigid intermediate tubular member 112 disposed therebetween. First articulatable segment 120 further includes first and second sections of articulating linkages 122, 124, respectively, interconnected by an elongated linkage 126. Similarly, second articulatable segment 140 includes first and second sections of articulating linkages 142, 144, respectively, interconnected by an elongated linkage 146. As can be appreciated, and as will be described in greater detail below, the various sections of linkages 122, 124, 142 and 144 permit articulation of cannula arm 100 to form various different configurations thereof, e.g., via selectively tensioning one or more of the sets of cables "C1" and "C3"-"C4."

More specifically, as best shown in FIG. 2A, cable set "C1" extends distally through tubular member 108, first linkage section 122, elongated linkage 126, and second linkage section 124, ultimately anchoring within intermediate tubular member 112. Although only one cable set "C1" is shown, it is envisioned that a pair of cable sets "C1" extend similarly through cannula arm 100 on one side thereof. Internal cable sets "CI" on the other hand, extend through first articulation segment 120, anchoring on either side thereof, but do not extend proximally (or distally) substantially beyond first articulation segment 120. In other words, internal cable sets "CI" are internal to first articulation segment 120, except for the anchoring thereof within elongated tubular member 108 and intermediate tubular member 112 at the ends thereof. Further, although only two opposed internal cable sets "CI" are shown, it is envisioned that four cable sets "CI" disposed at radially-spaced positions about cannula arm 100 be provided. As will be described below, cable set "C1" is selectively tensionable, e.g., via proximal articulation assembly 200 (FIG. 1), to articulate first articulatable segment 120.

With continued reference to FIG. 2A, opposed cable sets "C3" and "C4" each include a pair of cables. One of the cables of each of cable sets "C3" and "C4" extends distally through tubular member 108, first articulatable segment 120, intermediate tubular member 112, and first section 142 of second articulatable segment 140, ultimately anchoring in elongated linkage 146. The other cable of each cable set "C3" and "C4" extends distally through tubular member 108, first articulatable segment 120, intermediate tubular member 112, and second articulatable segment 140, ultimately anchoring in distal cap 110. However, although cable sets "C3" and "C4" extend through first articulatable segment 120, the tension on cable sets "C3" and "C4" is unaffected by the articulation or configuration of first articulatable segment 120, i.e., such that independence between first and second articulatable segments 120, 140, respectively, is maintained. The routing of cable sets "C3" and "C4" through first articulatable segment 120 to second articulatable segment 140 to maintain the independence between first and second articulatable segments 120, 140, respectively, will be described in detail below with reference to FIGS. 2E-2I, although this configuration applies similarly to the embodiment of FIGS. 2A-2D.

FIG. 2A shows cannula arm 100 disposed in a substantially straight configuration, wherein cannula arm 100 is substantially aligned with longitudinal axis "X-X." More particularly, both the first and second articulatable segments 120, 140, respectively, (and the first and second sections 122, 124 and 142, 144, respectively, thereof) are disposed in a substantially straight configuration. In this configuration, cable set "C1" is substantially un-tensioned such that the opposed cable sets "CI" are similarly tensioned to maintain first articulatable segment 120 in a straight configuration, i.e., such that first articulatable segment 120 does not curve, or bend off of longitudinal axis "X-X." Likewise, cable set "C3" and cable set "C4" are similarly tensioned relative to one another to achieve the same result, i.e., a straight configuration. As can be appreciated, this substantially straight configuration facilitates insertion of cannula arm 100 through an access port, e.g., access port 700 (FIGS. 13A-13F), disposed within an incision in tissue and into an internal surgical site.

Further, the links forming the first and second articulatable segments 120, 140, respectively, may be engaged to one another via springs (not explicitly shown) such that cannula arm 100 is biased toward this substantially straight position shown in FIG. 2A. As can be appreciated, due to this configuration, first articulatable segment 120 is returned to the substantially straight configuration when cable set "C1" is substantially un-tensioned.

FIG. 2B shows a second configuration of cannula arm 100, wherein both the first and second sections 142, 144, respectively, of second articulatable segment 140 are disposed in a fully articulated configuration such that the distal end 109 of cannula arm 100 is articulated, or curved off of longitudinal axis "X-X" and such that a distal surface 114 of cannula arm 100 faces generally perpendicularly to longitudinal axis "X-X." This configuration is achieved by applying greater tension to cable set "C3" as compared to cable set "C4" such that second articulatable segment 140 is curved off longitudinal axis "X-X" in the direction of cable set "C3." In this configuration, first articulatable segment 120, on the other hand, remains in the substantially straight configuration.

FIG. 2C shows a third configuration of cannula arm 100, wherein both the first and second sections 122, 124, respectively, of first articulatable segment 120 are disposed in a fully articulated configuration such that intermediate tubular member 112 is radially displaced from, but remains substantially parallel to, longitudinal axis "X-X" of cannula arm 100. This configuration is achieved by applying tension to cable set "C1" to articulate first linkage section 122 of first articulatable segment 120, as shown in FIG. 2C. As a result of this tension, the neutrality of tension between opposed internal cables "CI" is lost such that second linkage section 124 of first articulatable segment 120 is articulated in a substantially opposite direction relative to first linkage section 122, i.e., to form an S-like shaped configuration. In this configuration, second articulatable segment 140 remains in the substantially straight configuration, e.g., cable sets "C3" and "C4" are similarly tensioned, but is radially displaced from longitudinal axis "X-X" due to the articulation of first articulatable segment 120.

FIG. 2D shows a fourth configuration, wherein both the first and second articulatable segments 120, 140, respectively, are disposed in their respective fully articulated configurations, e.g., wherein cable set "C1" is tensioned and wherein cable set "C3" is more greatly tensioned as compared to cable set "C4." Similarly as in the previous configuration, in this fourth configuration, intermediate tubular member 112 is radially displaced from, but remains parallel to, longitudinal axis "X-X" of cannula arm 100. As can be appreciated, in this fourth configuration, cannula arm 100 defines a generally C-shaped configuration.

Turning now to FIGS. 2E-2F, another configuration for the cables extending through cannula arm 100 is shown. In the embodiment of FIGS. 2E-2F, a second cable set "C2" is added to oppose cable set "C1" such that, rather than tensioning and un-tensioning cable set "C1" to articulate and return first articulatable segment 120, first articulatable segment 120 is articulated or returned by applying greater or less tension, respectively, to cable set "C1" as compared to cable set "C2." In other words, cable set "C1" is tensioned to articulate first articulatable segment 120, while cable set "C2" is tensioned to return first articulatable segment 120 to the substantially straight configuration.

The configuration of cable sets "C3" and "C4" in FIGS. 2E-2F is substantially similar to that of the embodiment of cannula arm 100 described above with reference to FIGS. 2A-2D. In particular, one of the cables "$C3_1$," "$C4_1$" of each of cable sets "C3" and "C4," respectively, extends distally through tubular member 108, first articulatable segment 120, intermediate tubular member 112, and first section 142 of second articulatable segment 140, ultimately anchoring in elongated linkage 146, while the other cable "$C3_2$," "$C4_2$" of each cable set "C3" and "C4," respectively, extends distally through tubular member 108, first articulatable segment 120, intermediate tubular member 112, and second articulatable segment 140, ultimately anchoring in distal cap 110.

Turning now to FIGS. 2E-2I, as mentioned above, cable sets "C3" and "C4" are routed through first articulatable segment 120 such that the tension on cable sets "C3" and "C4" is unaffected by the articulation or configuration of first articulatable segment 120. More specifically, as shown in FIG. 2F, cable sets "C3" and "C4" are disposed at radially opposed positions about cannula arm 100 and are about 90 degrees offset from cable sets "C1" and "C2," respectively. An additional cable set is paired with each of cable sets "C3" and "C4" at the radially opposed positions thereof and extend through cannula arm 100 to second articulatable segment 140, e.g., such that four cable sets may be provided to permit 360 degree articulation of second articulatable segment 140. Due to this configuration, wherein cables sets "C3" and "C4" and the additional cable sets are offset 90 degrees relative to cable sets "C1" and "C2," the tension on cable sets "C3" and "C4" and the additional cable sets is not altered as cable sets "C1" and "C2" are selectively tensioned relative to one another to articulate first articulatable segment 120.

Referring now to FIGS. 2G-2I, once cable sets "C3" and "C4" and the additional cable sets extend through first articulatable segment 120 and into intermediate tubular member 112, cable sets "C3" and "C4" begin to rotate from the paired, opposed positions of FIGS. 2F and 2G, toward the position shown in FIG. 2I, wherein cable sets "C3," "C4," and the additional cable sets are equally-spaced radially about cannula arm 100 such that the four cable sets, cable sets "C3," "C4," and the additional cable sets, may be selectively tensioned to articulate second articulatable segment 140 through 360 degrees of articulation. In other words, the cable sets are bunched in pairs at opposed positions and are offset 90 degrees relative to cable sets "C1" and "C2" during passage through first articulatable segment 120 such that the tension on cable sets "C3" and "C4" is unaffected by the articulation or configuration of first articulatable segment 120, and cable sets "C3" and "C4" are rotated 90 degrees from this position as the cables extend from first articulatable segment 120 toward second articulatable segment 140 such that cable sets "C3" and "C4" and the additional cable sets are equally-spaced about cannula arm 100 to permit 360 degree articulation of second articulatable segment 140 via selective tensioning of one or more of the cable sets.

Figure 3:
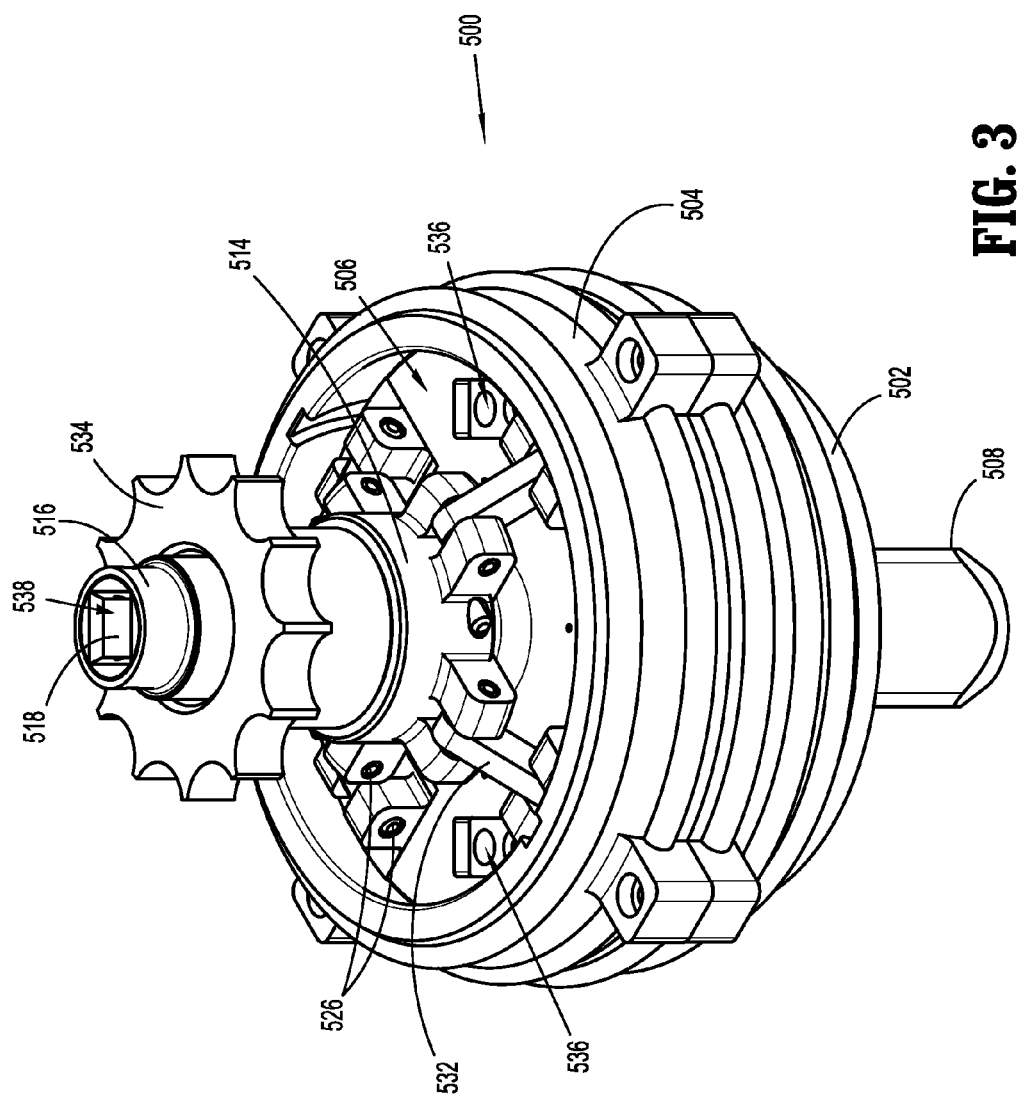
FIG. 3 is a perspective view of one embodiment of a gimbal assembly configured for use with the surgical access system of FIG. 1.
Figure 4:
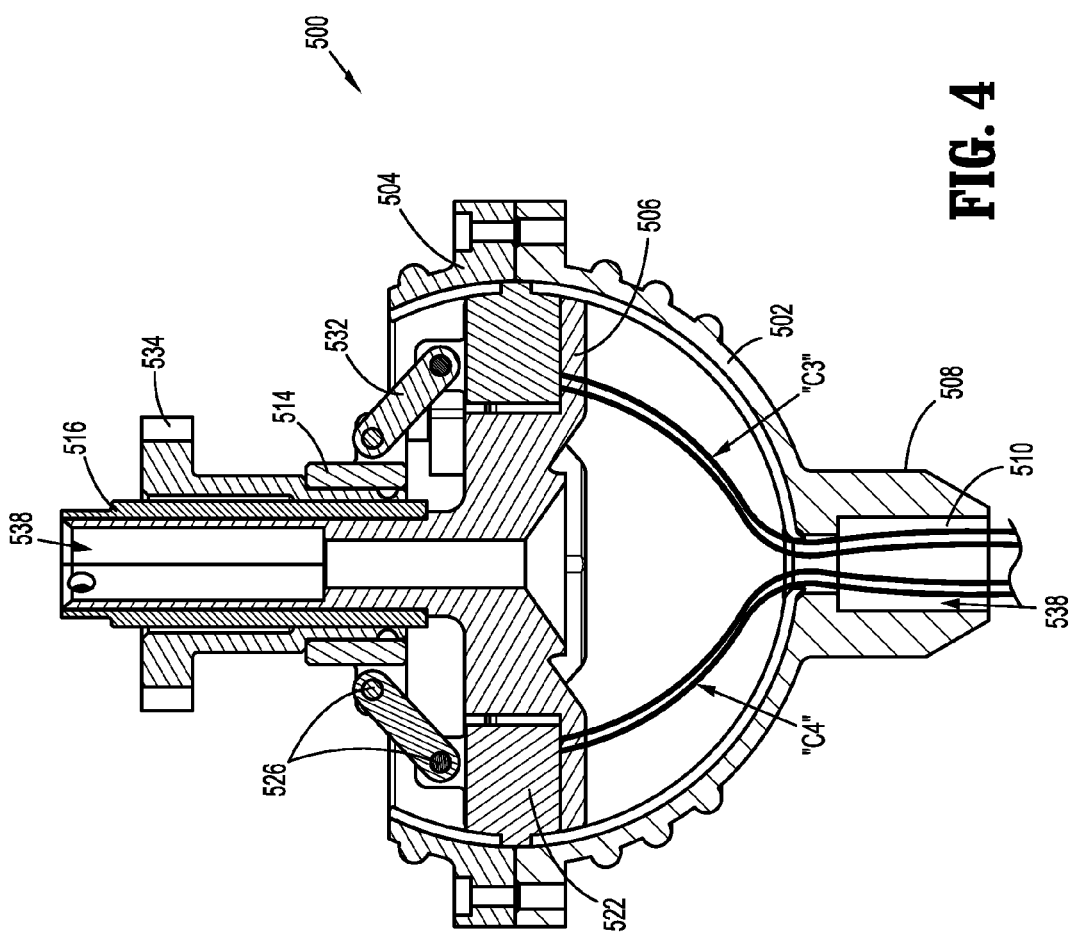
FIG. 4 is a side, cross-sectional view of the gimbal assembly of FIG. 3.

With reference now to FIGS. 3 and 4, one embodiment of a gimbal assembly configured for use with surgical access system 10 is shown generally identified by reference numeral 500. As will be described in detail below, gimbal assembly 500 is selectively manipulatable to articulate one of the articulatable segments of cannula arm 100, e.g., second articulatable segment 140, between the substantially straight configuration (see FIGS. 2A and 2C) and the curved, or articulated configuration (see FIGS. 2B and 2D).

Continuing with reference to FIGS. 3-4, gimbal assembly 500 includes a base member 502, a cover 504, and a rotatable member 506. Base member 502 has a semicircular or hemispherical configuration defining an internal cavity therein, although other configurations are contemplated. Base member 502 further includes a port 508 defining a passage 510 (FIG. 4) in communication with the cavity. Rotatable member 506 is disposed in the cavity. Rotatable member 506 is adapted to swivel or rotate within the cavity in multiple dimensions or along multiple axes with respect to base member 502 and cover 504. Cover 504 is attached to base member 502 to retain rotatable member 506 within the cavity of base member 502. Cover 504 may be attached to base member 502 through any conventional means including adhesives, bayonet coupling, or screws (as shown in FIG. 3).

Figure 5:
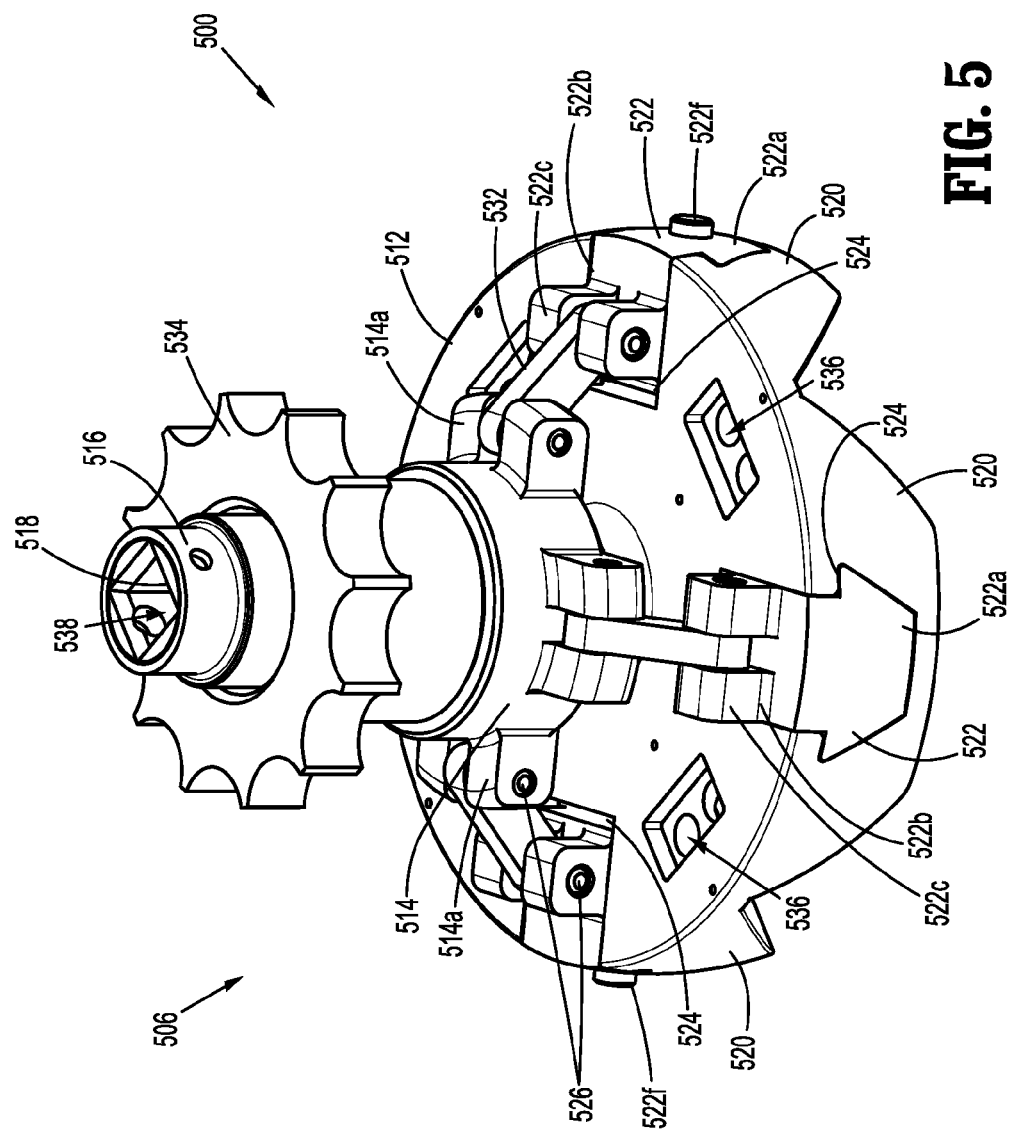
FIG. 5 is a perspective view of a rotatable member of the gimbal assembly of FIG. 3.

With reference now to FIG. 5, rotatable member 506 includes a base unit 512, a collar 514, and a neck 516. In particular, neck 516 extends proximally from base unit 512. Collar 514 is slidably mounted on neck 516 and is coupled to base unit 512. Neck 516 defines a channel 518 therethrough.

Channel 518 is in communication with the cavity defined in base member 502 (FIGS. 3-4), which in turn is in communication with passage 510 (FIG. 4) of port 508 (FIG. 4).

With continued reference to FIG. 5, in conjunction with FIGS. 3-4, base unit 512 of rotatable member 506 includes lateral walls 520 and locking fingers 522 circumferentially arranged about base unit 512. Lateral walls 520 conform to the contour of an inner surface of the semicircular or hemispherical-shaped base member 502. Specifically, lateral walls 520 extend radially inward to facilitate swivel or rotation thereof against the inner surface of base member 502. In addition, base unit 512 defines circumferentially arranged recesses 524, each of which at least partially extends along respective lateral wall 520. In particular, each recess 524 is adapted to accommodate therein at least a portion of locking finger 522. Each locking finger 522 includes a contact portion 522a and a head portion 522b. Head portion 522b includes a pair of protrusion members 522c defining a gap therebetween. Each protrusion member 522c defines a bore to accommodate a pin 526 therein.

Each locking finger 522 is movable between an unlocking state and a locking state. In the unlocking state, contact portion 522a of locking finger 522 is disposed in recess 524 defined in lateral wall 520 and is substantially flush with lateral wall 520 to enable swivel or rotation of rotatable member 506 with respect to base member 502 and cover 504. In the locking state, contact portion 522a of locking finger 522 extends radially outwardly from recess 524 defined in lateral wall 520 and contacts the inner surface of base member 502, such that pressure is applied against the inner surface of base member 502 by contacting portion 522a, thereby securing rotatable member 506 in a particular orientation with respect to base member 502 and cover 504. In addition, contact portion 522a may further include a gripping portion 522f to improve contact with and reduce slippage against the inner surface of base member 502, i.e., to facilitate the locking of rotatable member 506 in position relative to base member 502.

Figure 6:
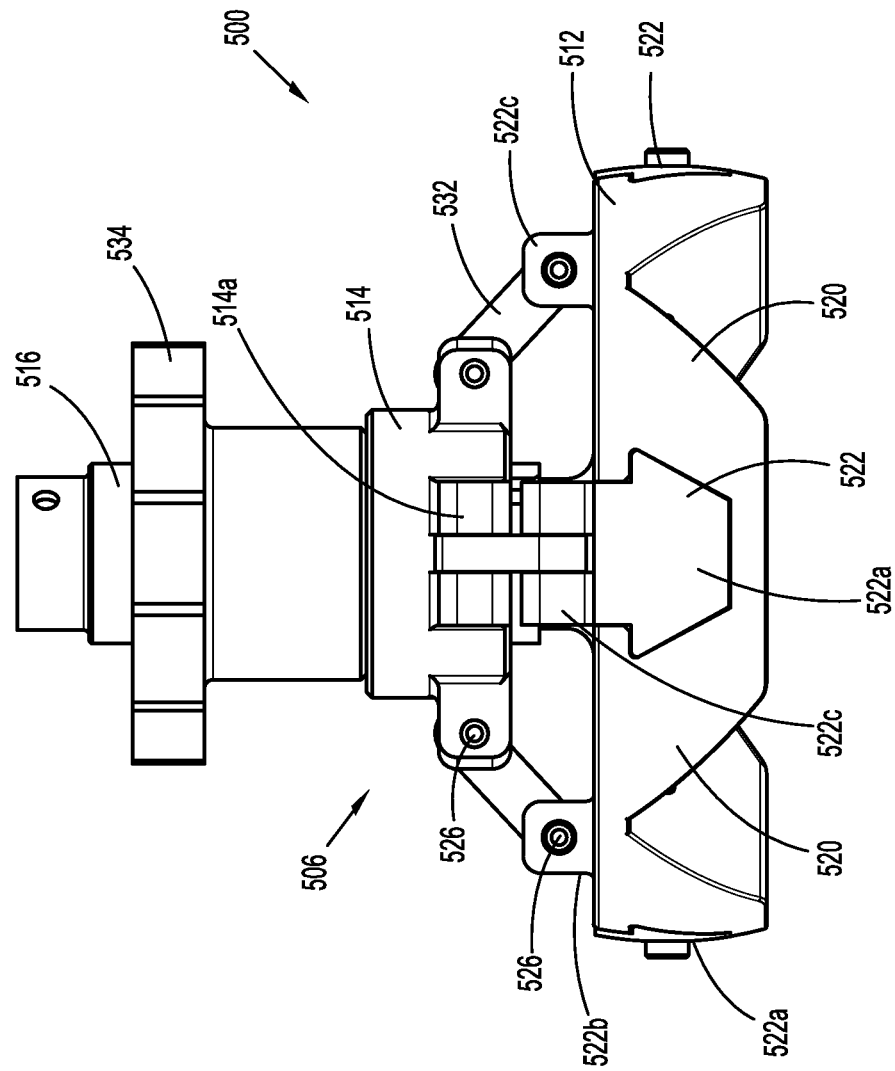
FIG. 6 is a side view of the rotatable member of FIG. 5.

With reference to FIGS. 5 and 6, in conjunction with FIGS. 3-4, collar 514 is translatably mounted on neck 516 of rotatable member 506. In particular, collar 514 includes a plurality of circumferentially arranged protruding parts 514a. Each pair of protruding parts 514a is aligned with a corresponding pair of protrusion members 522c of locking finger 522. Each locking finger 522 is coupled with collar 514 by a linkage member 532. Specifically, one end of linkage member 532 is received in the gap defined by the pair of protruding parts 514a of collar 514 and is pivotally connected to the pair of protruding parts 514a by a pin 526. The other end of linkage member 532 is pivotally disposed in the gap defined in head portion 522b of locking finger 522 and is pivotally connected to protrusion members 522c of locking finger 522 by pin 526. In this manner, the axial position of collar 514 along neck 516 determines the state of locking finger 522. For example, positioning locking collar 514 to the distal-most position along neck 516 causes linkage member 532 to urge head portion 522b of locking finger 522 such that locking finger 522 slides radially outwardly to urge contact portion 522a of locking finger 522 into contact with the inner surface of base member 502. In other words, positioning locking collar 514 in the distal-most position extends contact portion 522a of locking finger 522 radially outwardly to transition rotatable member 506 to the locking state.

With continued reference to FIGS. 5 and 6, in order to facilitate axial movement of collar 514 along neck 516 of rotatable member 506, rotatable member 506 further includes a lock wheel 534 threadedly mounted on neck 516. Neck 516 includes a corresponding threaded portion (not shown). Lock wheel 534 is coupled with collar 514, whereby rotation of lock wheel 534 about neck 516 moves lock wheel 534 and collar 514 axially along neck 516. In this manner, locking fingers 522 may be moved between the locking state and the unlocking state through rotation of lock wheel 534.

Figure 7:
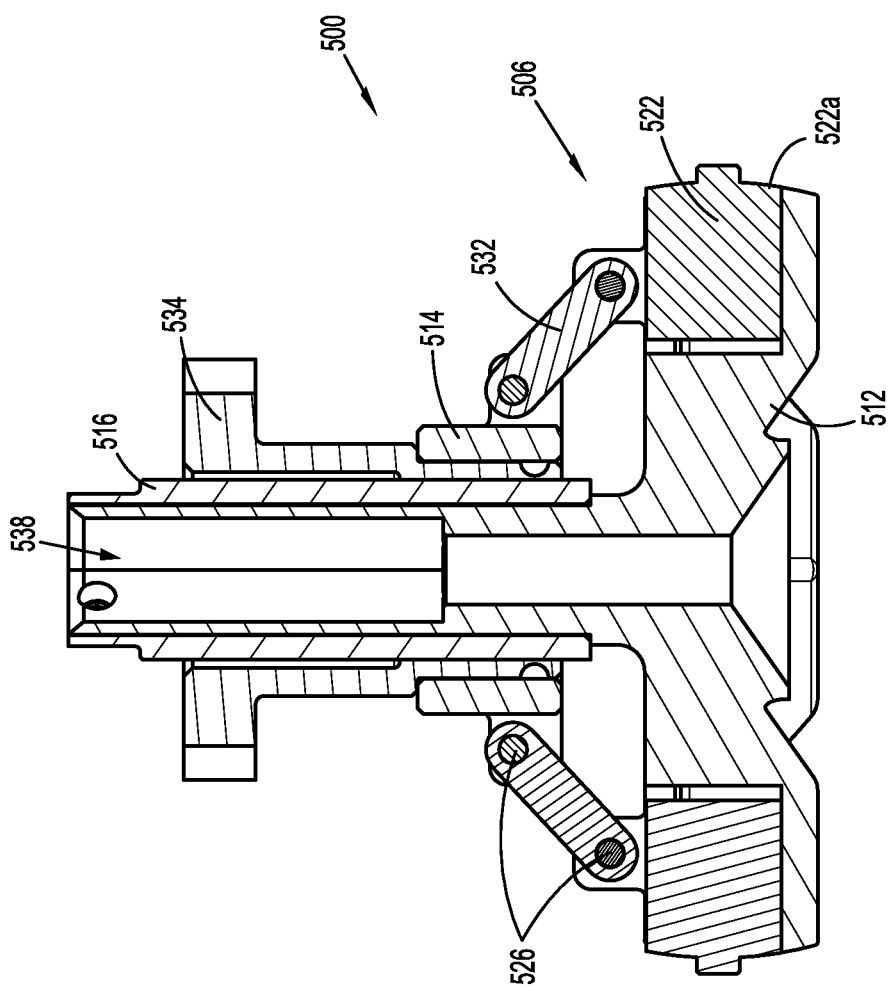
FIG. 7 is a side, cross-sectional view of the rotatable member of FIG. 5.

With reference to FIGS. 6 and 7, rotation of lock wheel 534 in a first direction moves collar 514 axially in the distal direction. Such movement transfers force to locking finger 522 through linkage member 532 which causes locking finger 522 to slide radially outwardly, enabling contact portion 522a to extend radially outwardly from recess 524 defined in base unit 512 such that locking fingers 522 are urged into contact with the inner surface of base member 502 (FIG. 4). In this manner, rotatable member 506 may be securely fixed in a desired orientation with respect to base member 502 and cover 504 (see FIGS. 3-4). Rotation of lock wheel 534 in a second direction (opposite of the first direction), on the other hand, moves collar 514 axially in the proximal direction. Such movement causes locking finger 522 to slide radially inwardly, returning contact portion 522a to within recess 524 defined in lateral wall 520, wherein contact portion 522a is substantially flush with lateral wall 520. In this manner, rotatable member 506 is able to freely rotate or swivel about various axes relative to base member 502 and cover 504 (see FIGS. 3-4).

Referring now to FIGS. 3-7, in conjunction with FIGS. 2A-2D, rotatable member 506 includes a plurality of engagement apertures 536 defined therethrough. Engagement apertures 536 are radially disposed about a center of rotatable member 506 and are configured to secure third and fourth cable sets "C3" and "C4," respectively, therein (although more engagement apertures 536 and cable sets may be provided to achieve greater degrees of articulation). In particular, third set of cables "C3" is engaged within one of the engagement apertures 536 and extends distally therefrom through cannula arm 100 and through second articulating segment 140 on a first side thereof, ultimately anchoring in distal cap 110 of cannula arm 100. Fourth set of cables "C4" is similarly engaged within another one of the engagement apertures 536 and extends distally therefrom through cannula arm 100 and through second articulating segment 140 on a second, opposed side thereof, ultimately anchoring in distal cap 110. Accordingly, in this configuration, as rotatable member 506 is swiveled or rotated within the cavity of base member 502, as described above, the opposed third and fourth sets of cables "C3," "C4," respectively, are selectively tensioned (or un-tensioned) relative to one another to articulate second articulatable segment 140 of cannula arm 100 between the substantially straight configuration (FIGS. 2A and 2C) and the articulated, or curved configuration (FIGS. 2B and 2D). Further, it is envisioned that engagement apertures 536 and the third and fourth sets of cables "C3," "C4," respectively, be oriented to translate rotation or movement of rotatable member 506 into similar articulation of second articulatable segment 140 of cannula arm 100. In other words, it is envisioned that moving rotatable member 506 in a first direction effects corresponding articulation of second articulatable segment 140 in that first direction.

Gimbal assembly 500 may further be transitioned between the locking state and the unlocking state, as described above, to retain rotatable member 506 in a desired orientation, thus retaining second articulatable segment 140, i.e., maintaining the relative tension between cable sets "C3" and "C4," of cannula arm 100 in a desired configuration, e.g., the substantially straight configuration, the articulated configuration, or any configuration therebetween.

Figure 8:
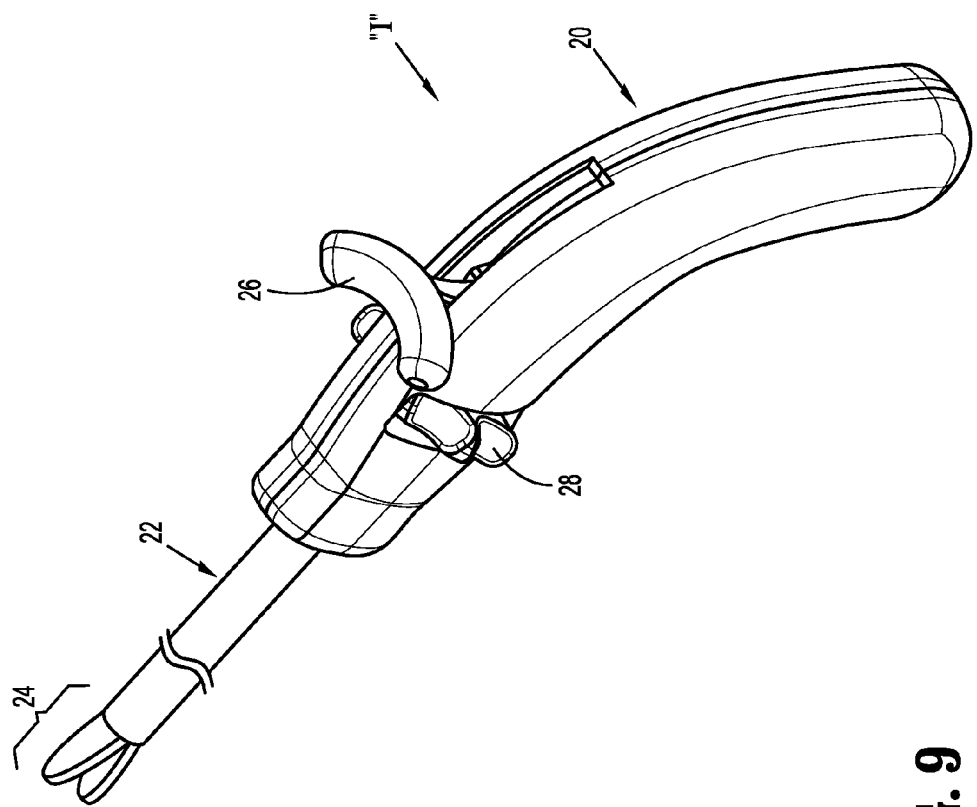
FIG. 8 is rear, perspective view of a surgical instrument configured for use with the surgical access system of FIG. 1.

Turning now to FIG. 8, in conjunction with FIGS. 1-4, an example of a surgical instrument configured for use with surgical access system 10 is shown as surgical instrument "I," although it is envisioned that any other suitable surgical instrument may be used in conjunction with surgical access system 10, depending on the surgical task to be completed. In particular, surgical instrument "I" includes a handle assembly 20, a flexible, elongated tubular member 22 extending distally from handle assembly 20 and an end effector assembly 24 (e.g., a pair of jaw members for grasping and/or manipulating tissue, or any other suitable end effector assembly for performing a surgical task within an internal surgical site) disposed at a distal end of the flexible, elongated tubular member 22. End effector assembly 24 of surgical instrument "I" is configured for insertion through longitudinal passageway 538 of gimbal assembly 500 and longitudinal passageway 104 of cannula arm 100 (which is in communication with longitudinal passageway 538 of gimbal assembly 500) such that end effector assembly 24 extends distally from distal cap 110 of cannula arm 100 within the internal surgical site. In this configuration, flexible elongated tubular member 22 of surgical instrument "I" is disposed within longitudinal passageway 104. Due to the flexible nature of elongated tubular member 22, elongated tubular member 22 is flexed, or curved in accordance with the articulation of cannula arm 100 to position end effector assembly 24 in a desired position and/or orientation. Further, surgical instrument "I" may be releasably engageable, i.e., lockable, with collar 514 of gimbal assembly 500 to retain surgical instrument "I" in substantially fixed position relative to rotatable member 506 thereof.

Figure 16:
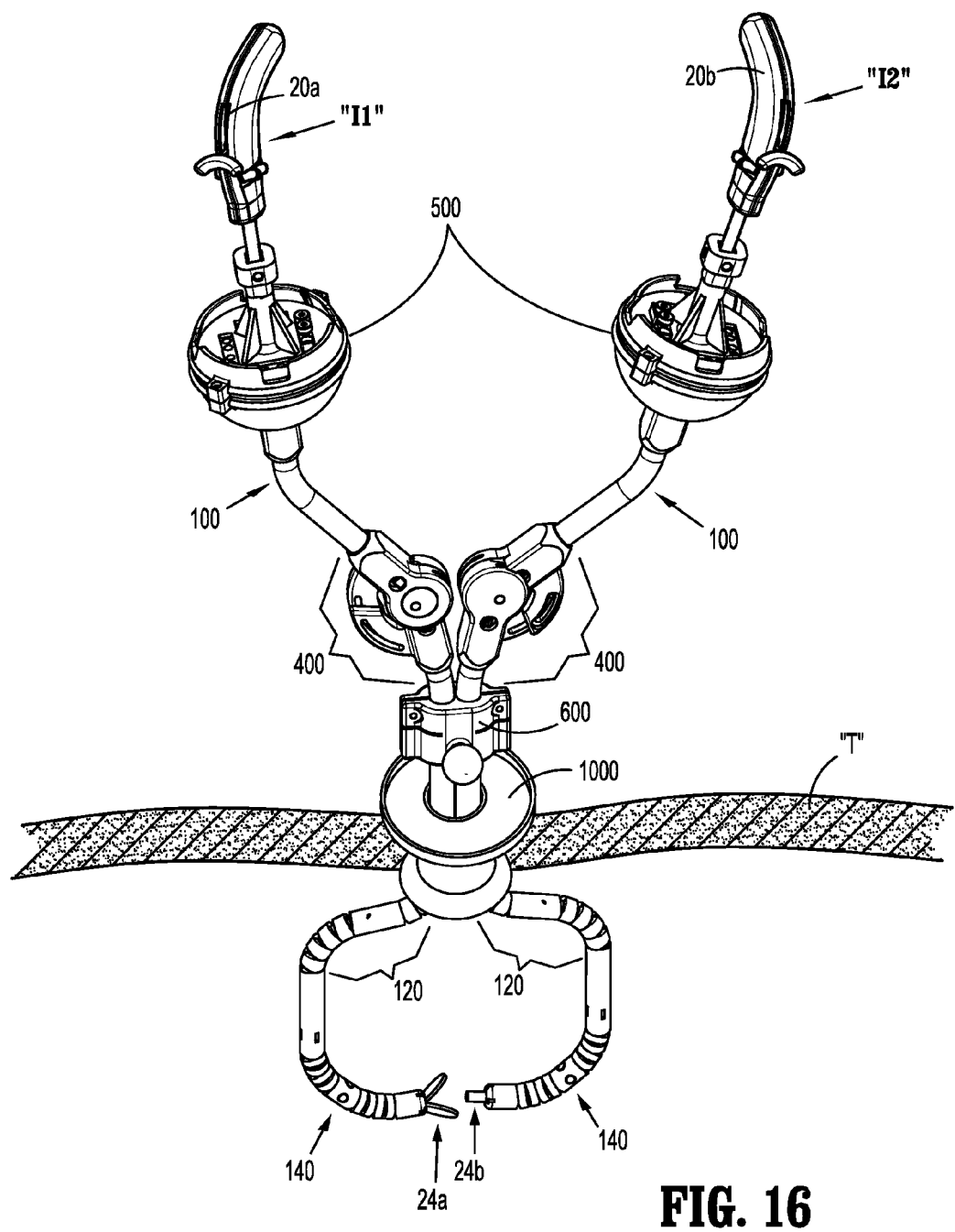
FIG. 16 is a top, perspective view of a surgical access system in accordance with the present disclosure inserted through an access port and into an internal surgical site.

With continued reference to FIGS. 1-4 and 8, in conjunction with FIG. 16, once surgical instrument "I" has been inserted into passageway 538 of gimbal assembly 500 and through passageway 104 of cannula arm 100 (and, optionally, locked to gimbal assembly 500), surgical instrument "I" may be manipulated to manipulate gimbal assembly 500 and, thus, to articulate second segment 140 of cannula arm 100, as desired. More specifically, manipulating handle assembly 20 of surgical instrument "I" urges rotatable member 506 to swivel or rotate within the cavity of base member 502, as described above, which, in turn, tensions (or un-tensions) cable sets "C3," "C4" to articulate second articulatable segment 140 of cannula arm 100. In other words, the surgeon may manipulate handle assembly 20 of surgical instrument "I" to effect corresponding articulation of cannula arm 100 and, thus, end effector assembly 24 which extends distally therefrom. As can be appreciated, handle assembly 20 remains disposed proximally and externally of surgical system 10, allowing the surgeon to grasp and manipulate surgical instrument "I" to articulate cannula arm 100 and also allowing the surgeon to manipulate trigger 26 and/or wheel 28 for further operating end effector assembly 24.

Figure 9:
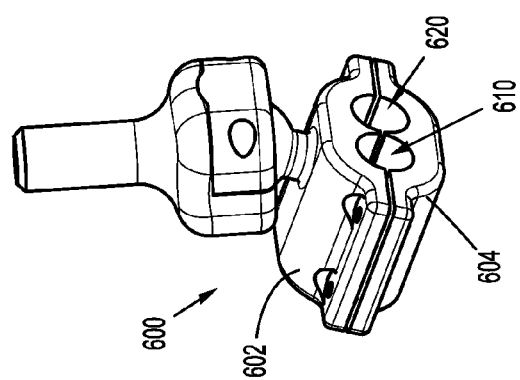
FIG. 9 is front, perspective view of a retainer clip configured for use with the surgical access system of FIG. 1.

Turning to FIG. 9, in conjunction with FIG. 1, a retaining clip 600 configured for use with surgical system 10 is shown. More specifically, retaining clip 600 is configured for positioning about first and second cannula arms 100 for retaining the substantially rigid tubular members 108 of the cannula arms 100 in fixed position relative to one another, e.g., such that the rigid tubular members 108 of cannula arms 100 are fixed in position adjacent to and substantially parallel relative to one another, although other configurations are contemplated. However, although retaining clip 600 couples the cannula arms 100 to one another, each of the cannula arms 100 remains independently articulatable.

With continued reference to FIG. 9, retaining clip 600 includes a pair of lumens 610, 620 extending therethrough. As can be appreciated, each lumen 610, 620 is configured to retain one of the cannula arms 100 therein. More specifically, retaining clip 600 includes first and second components 602, 604 that cooperate with one another to form lumens 610, 620. First and second components 602, 604 may be releasably engaged to one another via any suitable mechanism, e.g., screws, latching, etc., and may be adjustable relative to one another for increasing or decreasing the diameters of lumens 610, 620 to secure retaining clip 600 about cannula arms 600 or to permit retaining clip 600 to be slid longitudinally along cannula arms 600. In use, retaining clip 600 remains externally disposed of the body during a minimally-invasive surgical procedure.

Figure 10A:
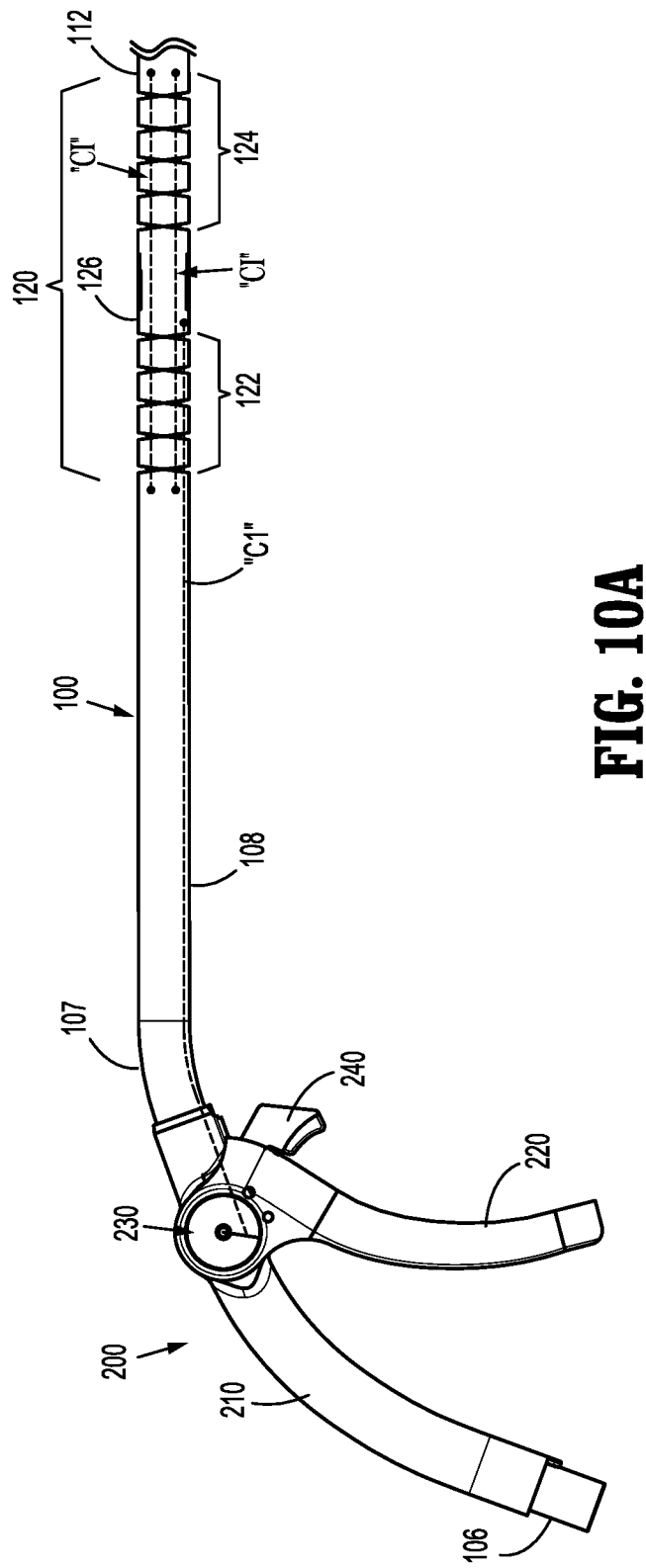
FIG. 10A is a side view of one embodiment of a lever-actuated articulation assembly configured for use with the surgical access system of FIG. 1.
Figure 10B:
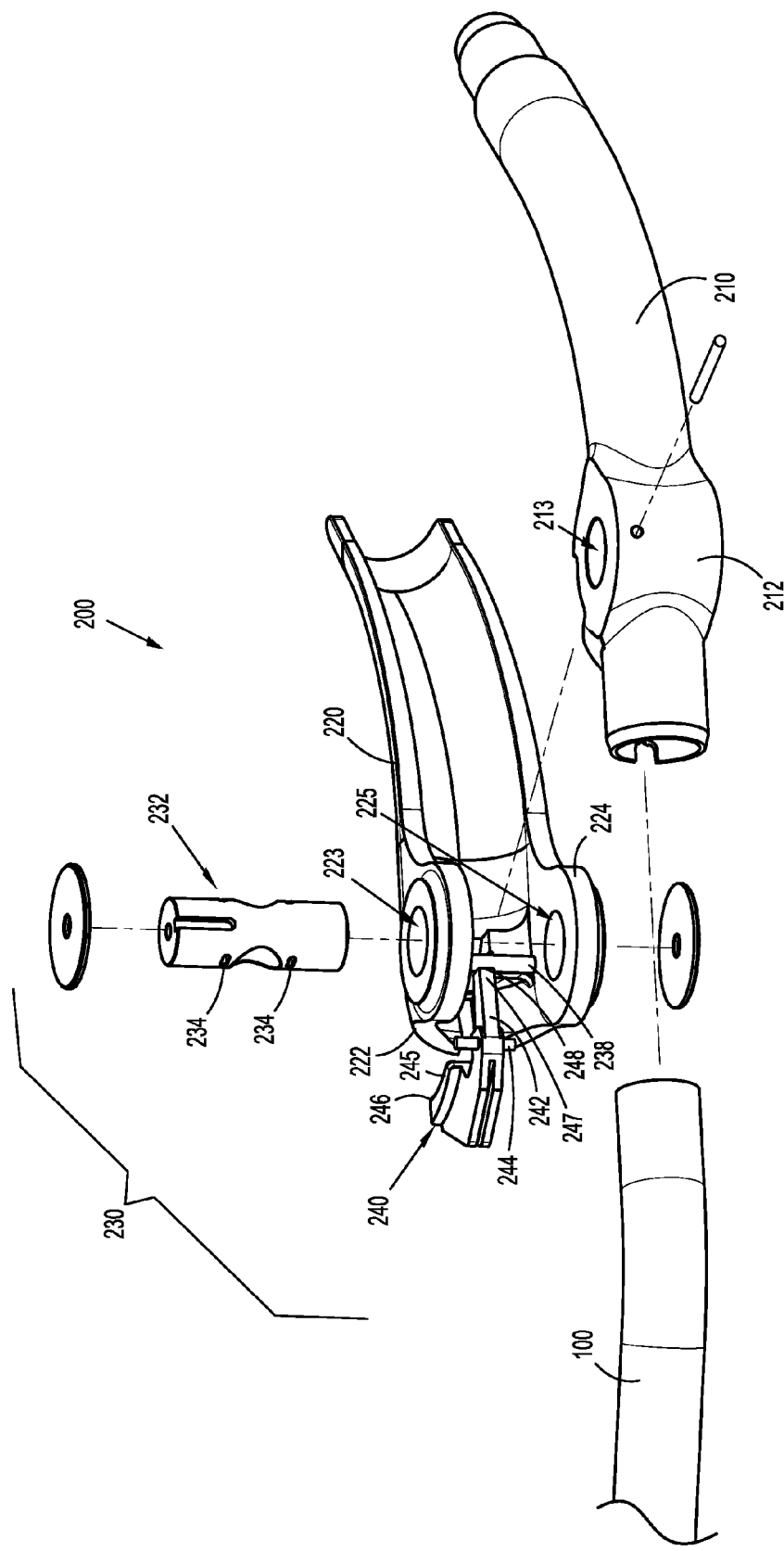
FIG. 10B is a side, exploded view of the lever-actuated articulation assembly of FIG. 10A.

Turning now to FIGS. 10A-10B, lever assembly 200 will be described. As mentioned above with reference to FIG. 1, lever assembly 200 is configured to selectively control the articulation of first articulatable segment 120 of cannula arm 100 between the substantially straight configuration (FIGS. 2A and 2B) and the articulated, or curved configuration (FIGS. 2C and 2D). More specifically, lever assembly 200 is disposed towards proximal end 106 of cannula arm 100 and includes a base portion 210 disposed about cannula arm 100, a lever arm 220 rotatable about a pivot assembly 230 relative to cannula arm 100 between a spaced-apart position and an approximated position, and a locking assembly 240. As shown in FIG. 10A, lever 220 may initially be disposed in the spaced-apart position such that first articulatable segment 120 of cannula arm 100 is initially disposed, or biased, toward the substantially straight configuration (also shown in FIGS. 2A and 2B), due to the lack of tension on cable set "C1" and the spring-biased configuration of the linkages of first articulatable segment 120. However, other configurations are also contemplated, e.g., wherein first articulatable segment 120 of cannula arm 100 is biased toward the articulated configuration (see FIGS. 2C and 2D). As will be described in greater detail below, moving lever 220 from the spaced-apart position toward the approximated position tensions cable set "C1" to articulate first section 122 thereof, which, in turn, unevenly tensions internal cable sets "CI" to articulate second section 124 thereof. In other words, moving lever 220 from the spaced-apart position toward the approximated position articulates first articulatable segment 120 of cannula arm 100 from the substantially straight configuration toward an articulated configuration (FIGS. 2C and 2D).

With continued reference to FIGS. 10A-10B, and to FIG. 10B in particular, lever 220 defines a cross-sectional configuration complementary to base portion 210 and defines a diameter slightly larger than that of base portion 210 such that, in the approximated position, lever 220 is disposed about base portion 210. Lever 220 further includes a pair of spaced-apart flanges 222, 224, each defining an aperture 223, 225, respectively, extending therethrough. Flanges 222, 224 are configured for positioned on either side of hub 212 of base portion 210, which includes a lumen 213 extending therethrough. During assembly, a pivot pin 232 is disposed through aperture 223 of flange 222, lumen 213 of hub 212, and aperture 225 of flange 224 to pivotably engage lever 220 and base portion 210 to one another. More specifically, pivot pin 232 is secured to flanges 222 and 224 such that movement of lever 220 between the spaced-apart and approximated positions rotates lever 220 relative to base portion 210 and rotates pivot pin 232 within and relative to hub 212 of base portion 210.

Pivot pin 232 further includes a pair of recesses 234 defined therein for securing the proximal ends of each of the cables of cable set "C1" thereto. The cables of cable set "C1" are secured within recesses 234 such that, upon rotation of pivot pin 232 relative to hub 212, the proximal ends of the cables of cable set "C1" are rotated about the pivot axis of pivot pin 232 to tension the cables of cable set "C1." Accordingly, as lever 220 is moved from the spaced-apart position to the approximated position to rotate pivot pin 232 relative to hub 212 of base portion 210, cable set "C1" is "wound-up" about pivot pin 232, thus pulling cable set "C1" proximally and tensioning cable set "C1." Due to this configuration, as lever 220 is moved toward the approximated position, first articulatable segment 120 of cannula arm is bent, or articulated from the substantially straight configuration (FIGS. 2A, 2B and 10A) to the curved, or articulated configuration (FIGS. 2C and 2D).

Referring momentarily to FIG. 1, and as mentioned above, cable sets "C3" and "C4" (FIGS. 2A-2D) are configured to extend from second articulatable segment 140 proximally through cannula arm 100, ultimately engaging gimbal assembly 500, which is manipulatable for selectively tensioning cable sets "C3" and "C3" (FIGS. 2A-2D) for articulating second articulatable segment 140. As such, cable sets "C3" and "C4" (FIGS. 2A-2D) pass through lever assembly 200. However, lever assembly 200 and pivot pin 232 thereof are configured such that cables "C3" and "C4" are uninterrupted, i.e., the tension on cables "C3" and "C4" is maintained, regardless of the position of lever 220 and/or locking assembly 240. This configuration maintains the independence of articulation between first and second articulatable segments 120, 140, respectively.

Referring again to FIGS. 10A-10B, locking assembly 240 includes a locking arm 242 pivotable about a pivot pin 244 secured within hub 212 of base portion 210 between an unlocked position and a locked position. Locking arm 242 includes a trigger 246 disposed at first end 245 thereof and a locking finger 248 disposed at second end 247 thereof. In use, upon movement of lever 220 to the approximated position relative to body portion 210 of lever assembly 200, i.e., to articulate first articulatable segment 120 of cannula arm 100 from the substantially straight configuration to the articulated configuration, locking finger 248 engages locking pin 238 of lever 220 to inhibit return of lever 220 to the spaced-apart position, thereby retaining pivot pin 232 in position and fixing the tension on cable set "C1." In other words, locking finger 248 engages locking pin 238 as lever 220 is approximated relative to base portion 210 such that lever 220 is locked in the approximated position, thereby locking first articulatable segment 120 of cannula arm 100 in the articulated position. Locking arm 242 may be biased by a spring (not shown) or other suitable biasing member such that locking finger 248 is biased into engagement with, i.e., automatically engages, locking pin 238 upon movement of lever 220 to the approximated position. Alternatively, locking arm 242 may be selectively actuatable, e.g., via depressing lock trigger 246, to lock lever 220 in position once lever 220 has reached the approximated position. As can be appreciated, in either configuration, lever 220 is freely movable from the spaced-apart position to just prior to the approximated position for moving first articulatable segment 120 of cannula arm 100 between the substantially straight and various partially-articulated positions. However, it is also envisioned that locking assembly 240 be configured to lock lever 220 in various positions between the spaced-apart and approximated positions for correspondingly locking first articulatable segment 120 of cannula arm 100 at various positions between the substantially straight configuration and the articulated configuration.

With continued reference to FIGS. 10A-10B, in order to unlock lever 220 from the approximated position (or any other position), trigger 246 of locking assembly 240 is depressed, thereby disengaging locking finger 248 and locking pin 238 and allowing lever 220 to return under bias back to the approximated position and, accordingly, rotating pivot pin 232 back to its initial position to substantially un-tension cable set "C1," thus returning first articulatable segment 120 of cannula arm 100 to the substantially straight configuration under the spring-bias of the linkages of first articulatable segment 120.

Figure 11A:
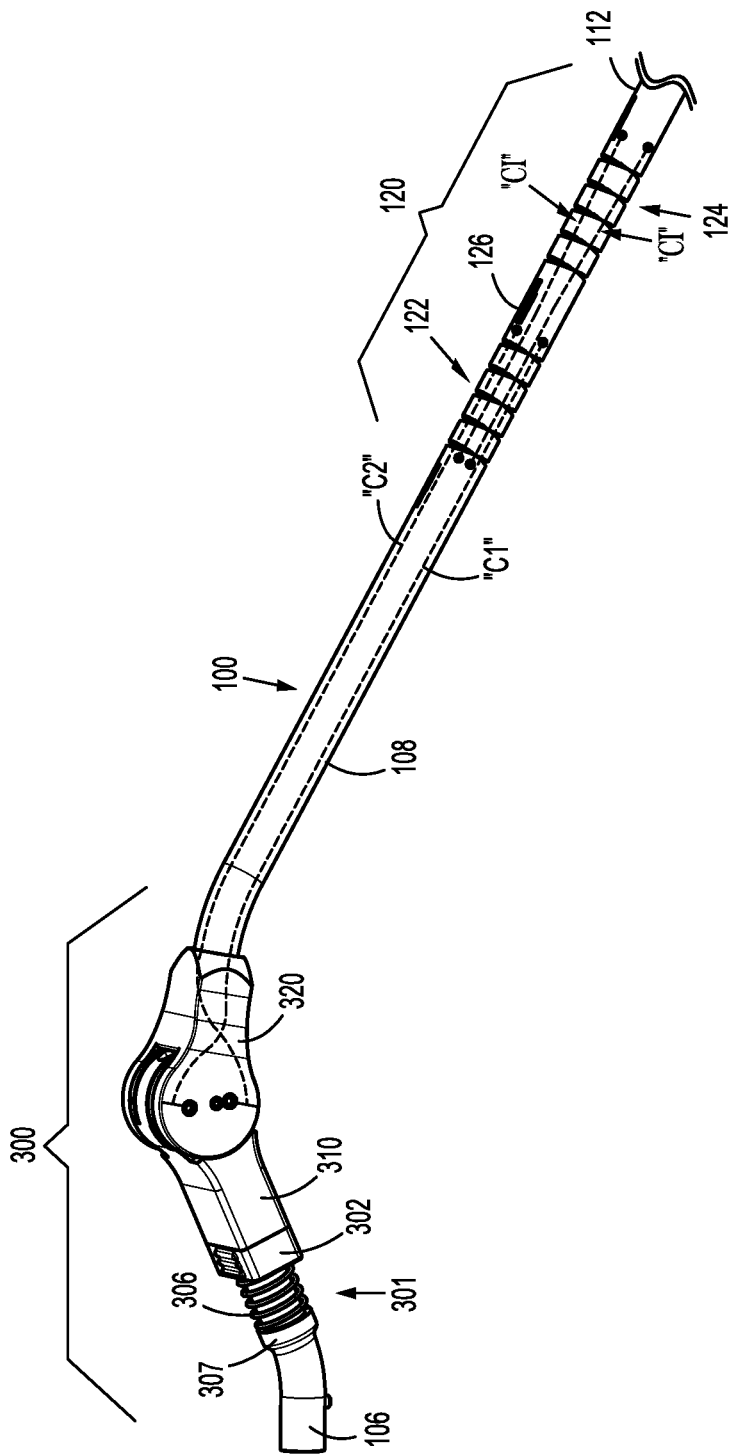
FIG. 11A is a perspective view of another embodiment of an articulation assembly configured for use with the surgical access system of FIG. 1.
Figure 11B:
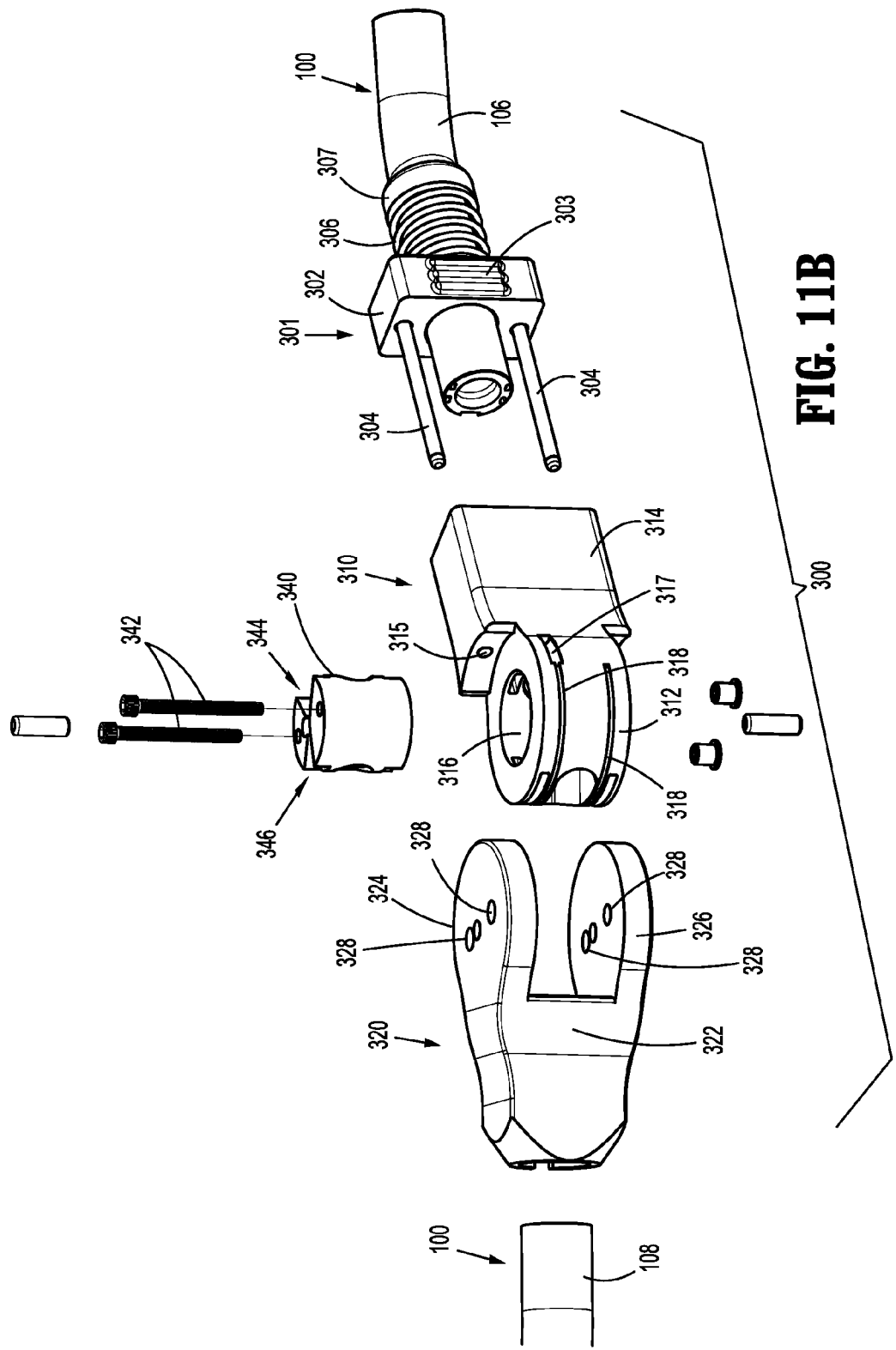
FIG. 11B is side, exploded view of the articulation assembly of FIG. 11A.

Referring to FIGS. 11A-11B, another embodiment of an articulation assembly for selectively controlling the articulation of first articulatable segment 120 of cannula arm 100 between the substantially straight configuration (FIG. 2E) and the articulated, or curved configuration (see e.g., FIGS. 2C and 2D), is shown designated as articulation assembly 300. Articulation assembly 300 incorporates the cable configuration shown in FIGS. 2E-2I, although other configuration, e.g., the configuration of FIGS. 2A-2D is also contemplated. Articulation assembly 300 is interdisposed between tubular member 108 of cannula arm 100 and proximal end 106 of cannula arm 100 and generally includes an inner member 310 and an outer member 320 pivotably coupled to inner member 310 such that inner member 310 is movable relative to outer member 320 between a substantially aligned position (see FIG. 11A), wherein the inner and outer members 310, 320, respectively, are substantially aligned with one another, and a substantially transverse position, wherein the inner and outer members 310, 320, respectively, are disposed in a substantially transverse relation relative to one another. As will be described in greater detail below, moving inner member 310 relative to outer member 320 from the substantially aligned position (FIG. 11A) to the substantially transverse position articulates first articulatable segment 120 of cannula arm 100 from the substantially straight configuration (FIGS. 2A, 2B and 11A) to the articulated configuration (FIGS. 2C and 2D).

Inner member 310 of articulation assembly 300, as best shown in FIG. 11B, includes a rotatable member 312 and a base 314 extending proximally therefrom. Rotatable member 312 is configured for positioning between flanges 322, 324 of outer member 320, as will be described below, and includes a central aperture 316 extending therethrough. Rotatable member 312 further includes a pair of recesses 317 defined within an outer periphery thereof and a channel 318 defined therein and extending circumferentially about rotatable member 312 from each of the recesses 317. The proximal end of each of cable sets "C1" and "C2" is secured within one of the recesses 317 of rotatable member 312 in opposite directions such that cable set "C1" extends from one of recesses 317 through corresponding channel 318 circumferentially about rotatable member 312 in a first direction, while cable set "C2" extends from the other recess 317 through the other channel 318 circumferentially about rotatable member 312 in a second, opposite direction. Due to this configuration, as will be described in greater detail below, rotation of inner member 310 relative to outer member 320 selectively tensions one of the cable sets, e.g., cable set "C1," while un-tensioning the other, opposed cable set, e.g., cable set "C2," thereby articulating first articulatable segment 120 of cannula arm 100 from the substantially straight configuration (FIGS. 2E and 10A) to the curved, or articulated configuration (see, e.g., FIGS. 2C and 2D).

Continuing with reference to FIGS. 11A-11B, outer member 320 of articulation assembly 300 includes a distal base 322 configured to engage tubular member 108 of cannula arm 100, and a pair of flanges 324, 326 extending proximally from distal base 322. Flanges 324, 326 are spaced-apart sufficiently to receive rotatable member 312 of inner member 310 therebetween. Flanges 324, 326 each include a plurality of apertures 328 defined therethrough. Apertures 328 are configured to receive bolts 342 therethrough. During assembly, boss 340 is positioned within central aperture 316 of rotatable member 312 of inner member 310 and outer member 320 is positioned about inner member 310 such that flanges 324, 326 are positioned on opposed ends of rotatable member 312 and boss 340. Thereafter, bolts 342 are inserted through apertures 328 and are secured within boss 340 to fixedly engage boss 340 between flanges 324, 326 of outer member 320. In this configuration, wherein boss 340 and outer member 320 are fixed in position relative to one another, inner member 310 is rotatable about boss 340 and, thus, relative to outer member 320 between the substantially aligned and substantially transverse positions. Boss 340 further includes a pair of detents 344, 346 defined therein, the importance of which will be described in greater detail below. Boss 340 also includes a passageway extending therethrough to permit insertion of a surgical instrument, e.g., surgical instrument "I" (FIG. 8), completely through cannula arm 100.

In use, as proximal end 106 of cannula arm 100 is moved radially, i.e., off-axis, relative to tubular member 108 of cannula arm 100, inner member 310 is rotated about boss 340 and relative to outer member 320 to permit such movement of proximal end 106 of cannula arm 100. This relative rotation of inner member 310 rotates rotatable member 312 such that cable set "C1" is wound-up about rotatable member 312, causing cable set "C1" to be pulled proximally, thereby tensioning cable set "C1." At the same time, cable set "C2" is un-wound about rotatable member 312, thereby slackening cable set "C2" to reduce the tension on cable set "C2." As a result, with a greater relative tension on first cable set "C1" as compared to second cable set "C2," first articulatable segment 120 of cannula arm 100 is articulated from the substantially straight configuration (FIGS. 2E and 11A) toward the articulated configuration (see, e.g., FIGS. 2C and 2D).

Referring still to FIGS. 11A-11B, articulation assembly 300 further includes a locking mechanism 301 for selectively locking inner and outer members 310, 320, respectively, in one of a plurality of fixed positions relative to one another. Locking mechanism 301 includes a block 302 having a pair of rods 304 extending distally therefrom. Rods 304 are configured to extend through lumens 315 defined within base 314 of inner member 310 and to protrude distally at least partially therefrom. More specifically, a spring 306 interdisposed between collar 307 and block 302 biases block 302 distally such that rods 304 are biased distally to protrude from lumens 315 of base 314 toward boss 340, which is disposed within central lumen 316 of rotatable member 312 of inner member 310.

In use, as inner member 310 is rotated relative to boss 340 and outer member 320 from the substantially aligned position toward the substantially transverse position to articulate first articulatable segment 120 of cannula arm 100, rods 304 are eventually positioned adjacent to first detent 344 defined within boss 340. With rods 304 positioned adjacent first detent 344, boss no longer inhibits further distal biasing of rods 304 and, as such, spring 306 urges block 302 and rods 304 distally such that rods 304 extend into first detent 344, thereby inhibiting rotation of boss 340 and inner member 310 relative to one another. In other words, the engagement between rods 304 and first detent 344 locks inner member 310 and outer member 320 in a first pre-determined position relative to one another and, thus, locks first articulatable segment 120 in a first articulated configuration.

In order to release inner and outer members 310, 320, respectively, from this locked position, block 302 is translated proximally to remove rods 304 from detents 344. In other words, block 302 serves as a release slide for locking mechanism 301. As such, block 302 may includes a gripping portion 303 (or gripping portions) configured to facilitate grasping and translating (i.e., sliding) block 302 against the bias of spring 306 to release locking mechanism 301. With rods 304 removed from detents 344, i.e., with block 302 in the release position, inner member 310 may be rotated relative to outer member 320, e.g., to a second pre-determined position, wherein rods 304 are positioned adjacent to second detent 346. Similarly as described above, once rods 304 are positioned adjacent to second detent 346, spring 306 urges rods 304 distally into second detent 346, thereby locking inner member 310 in the second predetermined position relative to outer member 320 and, accordingly, locking first articulatable segment 120 in a second articulated configuration.

As can be appreciated, the number and positioning of detents 344, 346 defined within boss 340 determine the number and position of pre-determined locking positions of inner and outer members 310, 320, respectively, and, thus, the locking configurations of first articulatable segment 120 of cannula arm 100. For example, inner and outer members 310, 320, respectively, may be initially biased towards the substantially aligned position such that first articulatable segment 120 of cannula arm 100 is biased toward the substantially straight configuration; detent 344 may be positioned to define an intermediate locking position of inner and outer members 310, 320, respectively, and, thus, an intermediate articulated configuration for first articulatable segment 120 of cannula arm 120; and detent 346 may be positioned at the substantially transverse position of inner and outer members 310, 320, respectively, such that the second locking position of inner and outer members 310, 320, respectively, locks first articulatable segment 120 of cannula arm 100 in the fully articulated configuration. However, it is envisioned that the number and position of detents 344, 346 may be altered to achieve other desired locking configurations for first articulatable segment 120 of cannula arm 100.

Referring briefly to FIG. 1, in order to maintain the independence of articulation between first and second articulatable segments 120, 140, respectively, cable sets "C3" and "C4" (FIGS. 2A-2D) are configured to extend through the passageway defined through boss 340 such that, similarly as discussed above with respect to articulation assembly 200, cables "C3" and "C4" are uninterrupted, i.e., the tension on cables "C3" and "C4" is maintained, regardless of the position inner and outer members 310, 320, respectively, relative to one another.

Figure 12A:
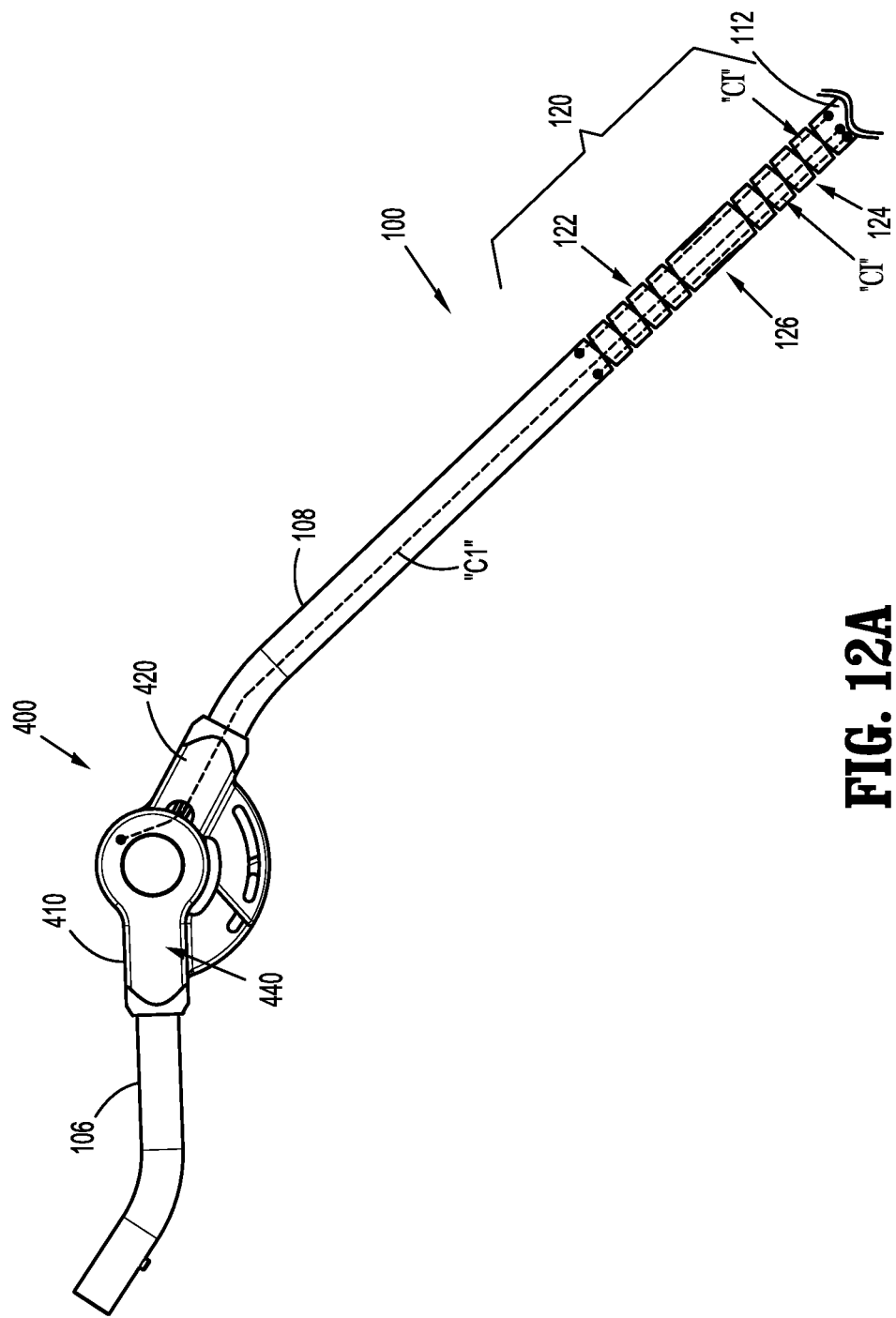
FIG. 12A is a perspective view of yet another embodiment of an articulation assembly configured for use with the surgical access system of FIG. 1.

With reference to FIGS. 12A-12C, yet another embodiment of an articulation mechanism 400 provided in accordance with the present disclosure and configured for use with surgical access system 10 (FIG. 1) is shown. Similar to the articulation mechanisms described above, articulation mechanism 400 is configured for selectively controlling the articulation of first articulatable segment 120 of cannula arm 100 between the substantially straight configuration (FIGS. 2A and 2B) and the articulated, or curved configuration (FIGS. 2C and 2D). More specifically, articulation mechanism 400 includes proximal and distal members 410, 420, respectively, that are pivotably movable relative to one another between a substantially aligned position (see FIG. 12A), wherein the proximal and distal members 410, 420, respectively, are substantially aligned with one another, and a substantially transverse position, wherein the proximal and distal members 410, 420, respectively, are disposed in a substantially transverse relation relative to one another, in order to articulate first articulatable segment 120 of cannula arm 100 between the substantially straight configuration (FIGS. 2A and 2B) and the articulated configuration (FIGS. 2C and 2D).

Proximal member 410 of articulation assembly 400 includes a connector 412 configured for engagement with proximal end 106 of cannula arm 100, a semi-disc-shaped flange 414 extending from connector 412, and an annular central member 416 extending distally from connector 412. The curvature of semi-disc-shaped flange 414 is similar to that of central member 416 such that semi-disc-shaped flange 414 is co-axially positioned relative to central member 416 along the length of semi-disc-shaped flange 414. Further, semi-disc-shaped flange 414 includes an arcuate slot 415 defined therethrough that defines a similar arc-angle as compared to semi-disc-shaped flange 414. Central member 416, on the other hand, includes a central aperture 417 defined therethrough. As best shown in FIGS. 12A and 12B, the proximal ends of the cables of cable set "C1" are anchored within central member 416 at a radially-spaced position, i.e., off-center, relative to central aperture 417. Proximal member 410 may further include a cap 440 disposed thereon that includes a knob 430*a* extending into central aperture 417. Knob 430*a* is centered relative to cannula arm 100, the importance of which will be described in greater detail below.

Distal member 420 is similar to proximal member 410 and includes a connector 422 configured for engagement with tubular member 108 of cannula arm 100, a semi-disc-shaped flange 424 extending from connector 422, and an annular central member 426 extending proximally from connector 422. As with proximal member 410, semi-disc-shaped flange 424 is co-axially positioned relative to central member 426 along the length of semi-disc-shaped flange 424. Semi-disc-shaped flange 424 also includes an arcuate slot 425 defined therethrough that defines a similar arc-angle as compared to semi-disc-shaped flange 424. Central member 426 of distal member 420 includes a central recess 427 defined therein that is configured for positioning about and in alignment with central aperture 417 of central member 416 of proximal member 410. Recess 427 includes a recessed floor 428 that includes a knob 430*b* extending therefrom that opposes knob 430*a* of cover 440 of proximal member 410, but is sufficiently spaced therefrom to permit passage of a surgical instrument therebetween. Further, cable set "C1" is configured to extend through connector 422 of distal member 420 and into anchored engagement within central member 416 of proximal member 410 at a radial position thereof, as best shown in FIG. 12B.

In the assembled condition, as shown in FIG. 12B, proximal member 410 is positioned substantially atop distal member 420, although flange 424 of distal member 420 is disposed atop flange 414 of proximal member 410, and such that central members 416, 426, respectively, thereof are aligned with one another. Proximal and distal members 410, 420, respectively, are coupled to one another in any suitable fashion that permits relative rotation of proximal and distal members 410, 420 between the substantially aligned position and the substantially transverse position, e.g., via a pin (not explicitly shown) engaged within slots 415, 425 of flanges 414, 424, respectively, of proximal and distal members 410, 420, respectively.

In use, as proximal end 106 of cannula arm 100 is moved radially, i.e., off-axis, relative to tubular member 108 of cannula arm 100, proximal member 410 is rotated relative to distal member 420. As proximal member 410 is rotated relative to distal member 420, central member 416 of proximal member 410 is rotated relative to central member 426 of distal member 420 such that cable set "C1" is pulled proximally (due to its anchoring within central member 416 of proximal member 410 and the rotation of central member 416), causing cable set "C1" to be tensioned. As a result, with cable set "C1" tensioned, first articulatable segment 120 of cannula arm 100 is articulated from the substantially straight configuration (FIGS. 2A and 2B) toward the articulated configuration (FIGS. 2C and 2D), similarly as described above with respect to lever assembly 200 (FIGS. 10A-10B).

As mentioned above, knobs 430*a*, 430*b* extend into the passageway defined through articulation assembly 400. More specifically, knobs 430*a*, 430*b* are configured to route cable sets "C3" and "C4" (FIGS. 2A-2D), respectively, therearound. Since knobs 430*a*, 430*b* are centrally disposed relative to cannula arm 100, the tension on cable sets "C3" and "C4" (FIGS. 2A-2D) is not altered as proximal and distal members 410, 410 are rotated relative to one another between the substantially aligned and substantially transverse positions. In other words, knobs 430*a*, 430*b* help maintain the independence between the articulation of first and second articulatable segments 120, 140, respectively (see FIG. 1).

Figure 13B:
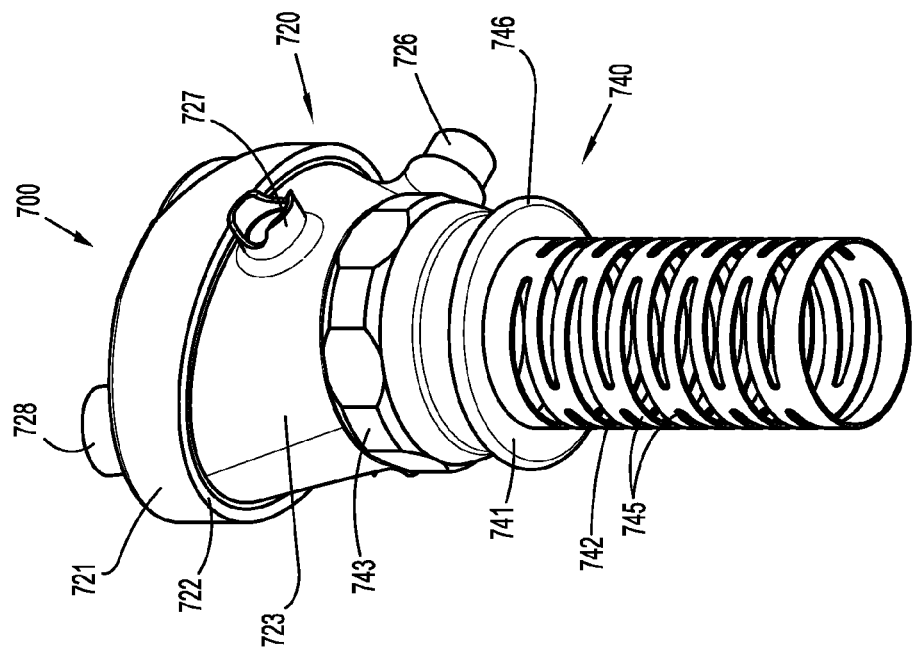
FIG. 13B is a bottom, perspective view of the surgical portal apparatus of FIG. 13A.
Figure 13A:
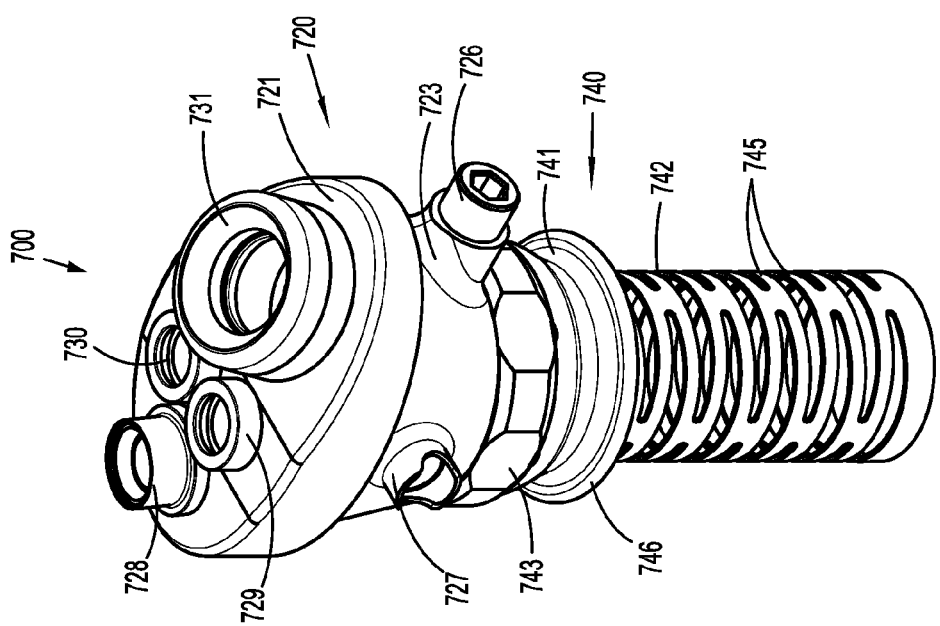
FIG. 13A is a top, perspective view of one embodiment of a surgical portal apparatus configured for use with the surgical access system of FIG. 1.

Referring now to FIGS. 13A-13F and initially to FIGS. 13A-13B, one embodiment of a surgical portal apparatus 700 configured for use with surgical access system 10 is shown. Surgical portal apparatus 700 generally includes a housing 720 and a tubular member 740. Surgical portal apparatus 700 is adapted for insertion within an incision in tissue, e.g., through the abdominal or peritoneal lining, in connection with a laparoscopic or endoscopic surgical procedure and is dimensioned to receive surgical objects therethrough to provide access to an internal surgical site. Housing 720 is configured to be releasably attached to tubular member 740, although housing 720 and tubular member 740 may alternatively be permanently attached or affixed to one another in any suitable manner. Housing 720 and tubular member 740 may also be utilized independently with other surgical objects such as, for example, an obturator, as will be discussed below.

Figures 13C, 13D:
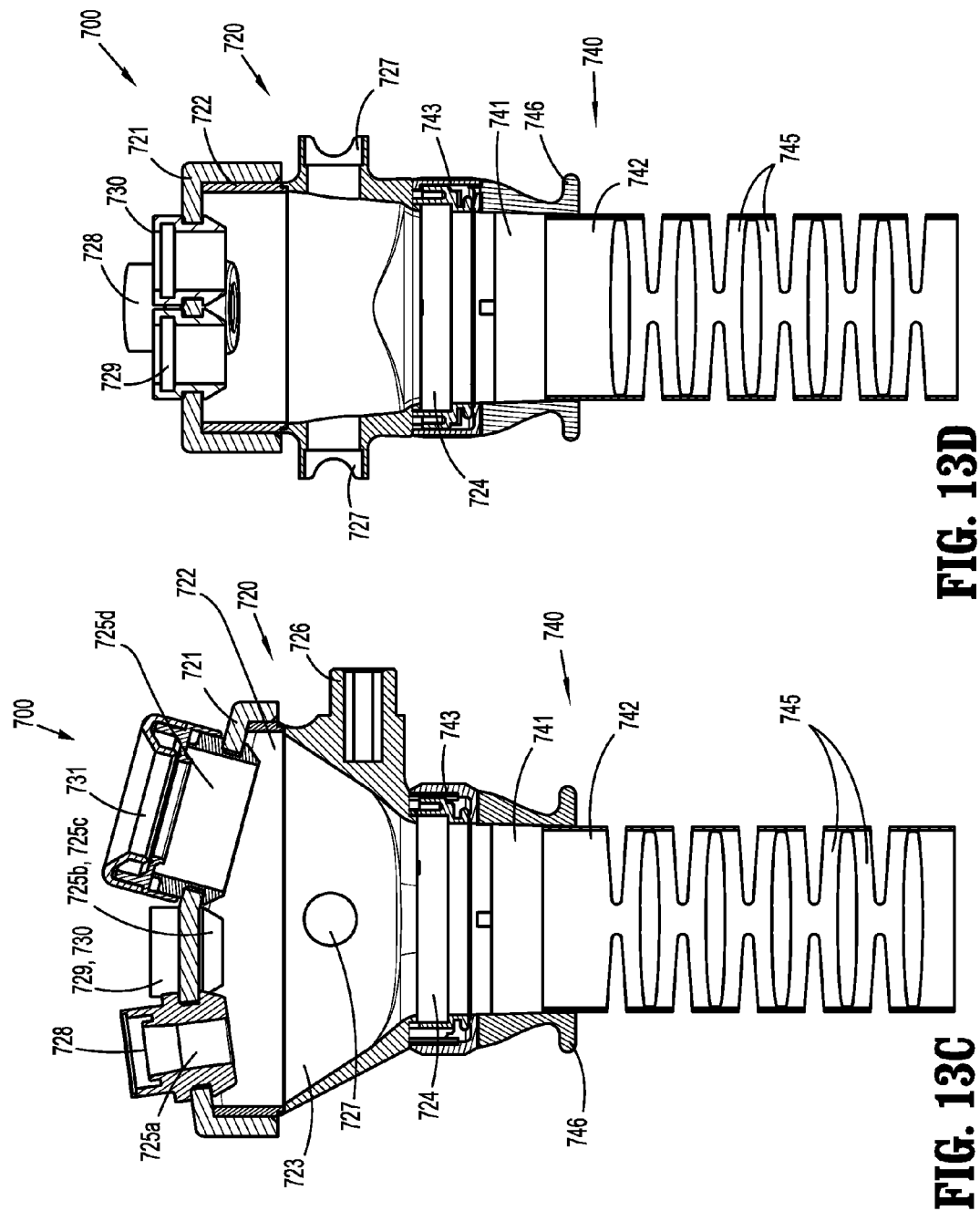
FIG. 13C is a side, cross-sectional view of the surgical portal apparatus of FIG. 13A.
FIG. 13D is a front, cross-sectional view of the surgical portal apparatus of FIG. 13A.

Referring now to FIGS. 13C-13D, housing 720 includes a cover 721, a cap piece 722, a central portion 723, and a locking connector 724. Cover 721 is disposed at the proximal end of housing 720 and defines a plurality of passageways 725*a*-725*d* for the reception of surgical objects. Cover 721 may be formed from any foam, rubber or gel like material which is adapted to flex or move upon manipulation of a surgical object so as to allow a surgeon a greater range of motion. Passageways 725*a*-725*d* are configured and dimensioned to accommodate a variety of differently sized surgical objects and may include sealing ports 728-731 to allow for the maintenance of a fluid-tight sealed surgical space. Sealing ports 728-731 may be formed monolithically or may be formed of separate parts. Sealing port 731 may include a mounting ring 731*a*, a valve ring 731*b*, and a valve member 731*c*. Mounting ring 731*a* is adapted to form a sealed relationship with cover 721 and dimensioned to receive valve ring 731*b* in a substantially fluid sealed manner. Valve ring 731*b* is adapted to receive valve member 731*c* in a fluid sealed manner. Sealing ports 728-731 may include sealing valves for maintenance of a fluid tight seal such as flapper valves, duckbill valves, or other suitable valves. Although four passageways 725*a*-725*d* and sealing ports 728-731 are shown it is envisioned that cover 721 may include alternate configurations containing larger or smaller numbers and sizes of passageways 725*a*-725*d* and sealing ports 728-731 depending on the needs of the surgeon. In one particular example, each of the cannula arms 100 of surgical access system 10 is inserted through one of sealing ports 729, 730 (which define similar configurations), while the remaining ports 728, 731 may be used for other instrumentation or may simply be left vacant.

Cap piece 722 is dimensioned to receive cover 721 in a fluid sealed manner and to attach cover 721 to central portion 723. Central portion 723 may include a connector 726 and a fluid conducting conduit 727. Connector 726 is adapted to releasably couple housing 720 to a surgical support system (not shown) for maintaining surgical portal apparatus 700 securely in position, while fluid conducting conduit 727 provides fluid access to and from the internal surgical site. Fluid conduit 727 may include a valve (not shown) in fluid communication therewith for controlling the rate and/or direction of fluid flow therethrough. Fluid conducting conduit 727, for example, may be used to introduce insufflation gasses into the internal body cavity. Locking connector 724 is attached at the distal end of central portion 723 and is adapted for releasable attachment to tubular member 740 via snap fit, bayonet coupling, screw fit or other suitable mechanism. It is also envisioned that at least some of the components of housing 720 may be monolithically formed, including but not limited to cap piece 722, central portion 723 and locking connector 724.

Tubular member 740 includes a body connector 741, a flexible portion 742, and a locking collar 743. Tubular member 740 defines a passageway therethrough and may also include a sealing valve to maintain insufflation when housing 720 is removed. Body connector 741 is disposed at the proximal end of flexible portion 742 and locking collar 743 is disposed at the proximal end of body connector 741. Body connector 741 and locking collar 743 may also be monolithically formed. Locking collar 743 is dimensioned to releasably receive locking connector 724 of housing 720 via a bayonet coupling in a substantially fluid sealed manner. Locking collar 743 may alternatively receive locking connector 724 in snap fit, screw fit or any other suitable arrangement. Locking connector 724 may include a sealing mechanism 733 such as, for example, an o-ring, to facilitate attachment to locking collar 743 in a substantially fluid sealed manner.

Flexible portion 742 is dimensioned and configured for insertion into an incision whereby flexible portion 742 creates a substantially sealed relationship with the incision. Flexible portion 742 is adapted to allow surgical objects access through the incision and into the surgical space. Flexible portion 742 is formed of a flexible material that is capable of deforming during manipulation of surgical objects while still maintaining seal integrity in the surgical space and may be made from suitable biocompatible polymers. Flexible portion 742 may include a plurality of ribs 745 which facilitate the flexing of flexible portion 742 while providing additional structural strength. Ribs 745 may be formed of the same material as flexible portion 742 or may be formed of a different material. Flexible portion 742 may also include a tubular segment (not shown) internal or external to the ribs which facilitates the sealed reception of flexible portion 742 in the tissue. The tubular segment (not shown) and ribs 745 may also be formed monolithically. Further, flexible portion 742 may be capable of deforming upon insertion into an incision in tissue to substantially conform to the shape of the incision and thereby provide a better seal.

Figure 13F:
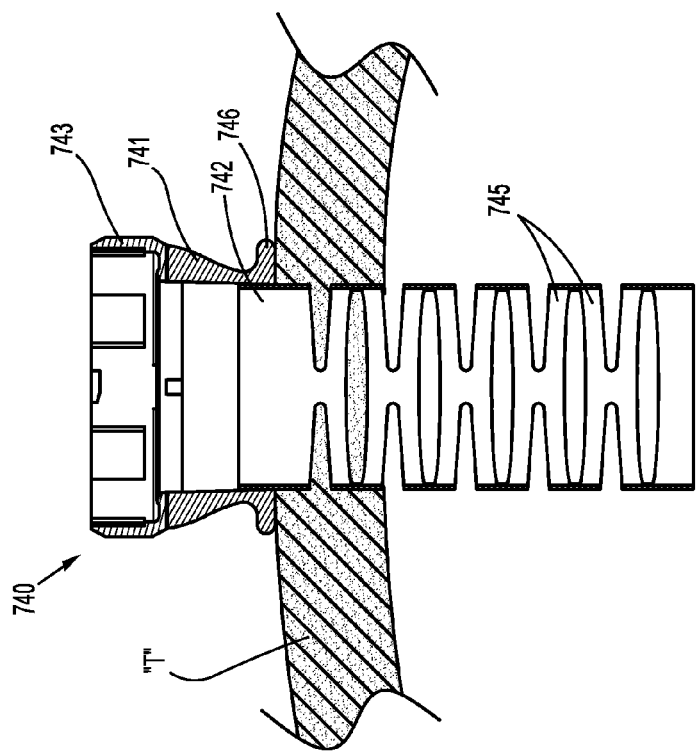
FIG. 13F is a side, cross-sectional view of the surgical portal apparatus of FIG. 13A inserted into an incision in tissue with the obturator removed therefrom.
Figure 13E:
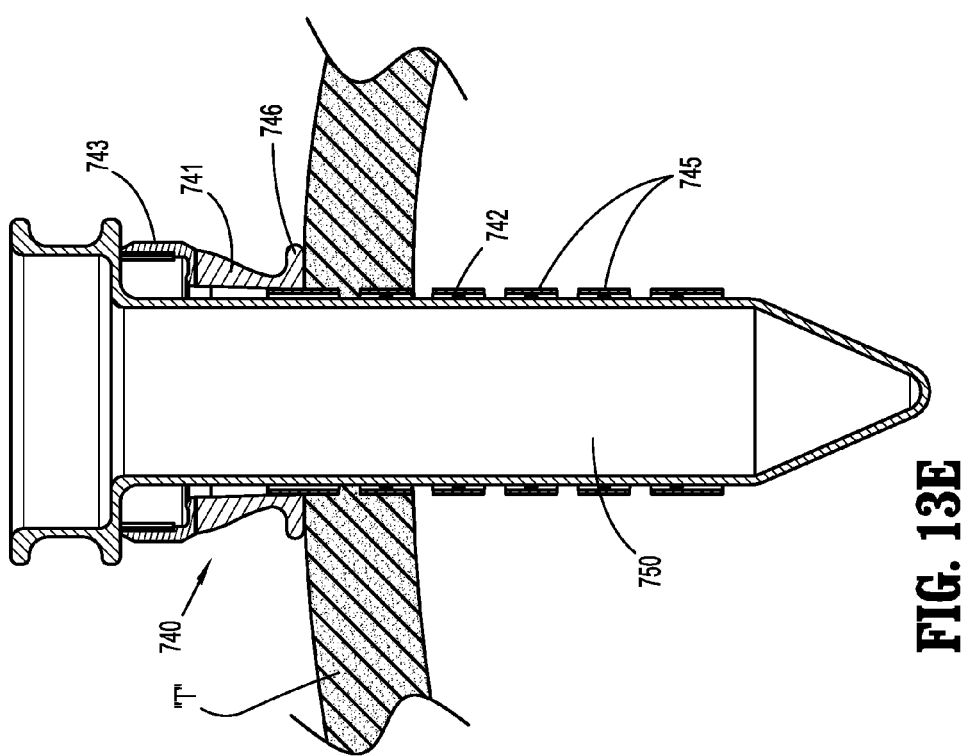
FIG. 13E is a side, cross-sectional view of the surgical portal apparatus of FIG. 13A inserted into an incision in tissue with an obturator inserted therethrough.

Referring now to FIGS. 13E-13F, body connector 741 may include a flange 746 disposed at the distal end of body connector 741. Flange 746 may be used to indicate to a surgeon or physician that tubular member 740 is fully inserted into the incision and may also be adapted to provide a sealing relationship with an outer wall of tissue "T." Flange 746 may be formed of the same material as body connector 741 or may be formed of a foam like or other material suitable for creating a fluid tight seal with tissue "T." Optionally flange 746 may include a separate material attached thereto to facilitate the creation of the sealed relationship with tissue "T."

During use, referring now to FIGS. 13A-13F, with housing 720 detached from tubular member 740, obturator 750 is inserted into tubular member 740. Tubular member 740 is then inserted into an incision in tissue "T" until flange 746 rests against the outer wall of tissue "T." Once tubular member 740 is fully inserted, obturator 750 is removed and housing 720 is attached. Alternatively, tubular member 740 may be inserted into the incision in tissue "T" without obturator 750. In this case housing 720 may be attached either prior to insertion or after insertion. After housing 720 is attached to tubular member 740 by inserting locking connector 724 into locking collar 744 a surgical object may be introduced through one of the passageways 725*a*-725*d* and into the surgical space. For example, each of the cannula arms 100 of surgical access system 10 (FIG. 1) may be inserted through one of the sealing ports 729, 730.

Figure 14A:
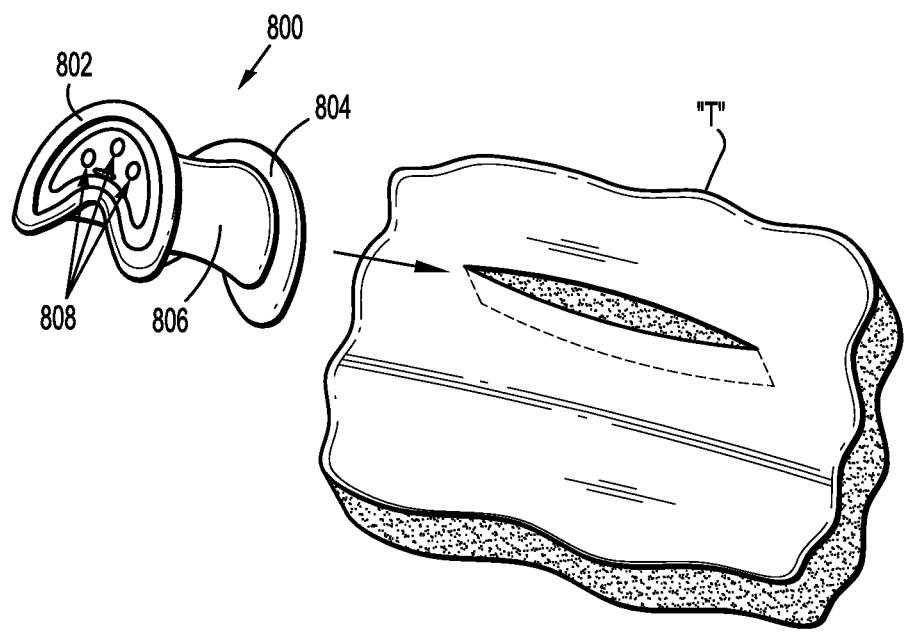
FIG. 14A is top, perspective view of another embodiment of a surgical access port configured for use with surgical access system of FIG. 1 in position for insertion into an incision in tissue.
Figure 14B:
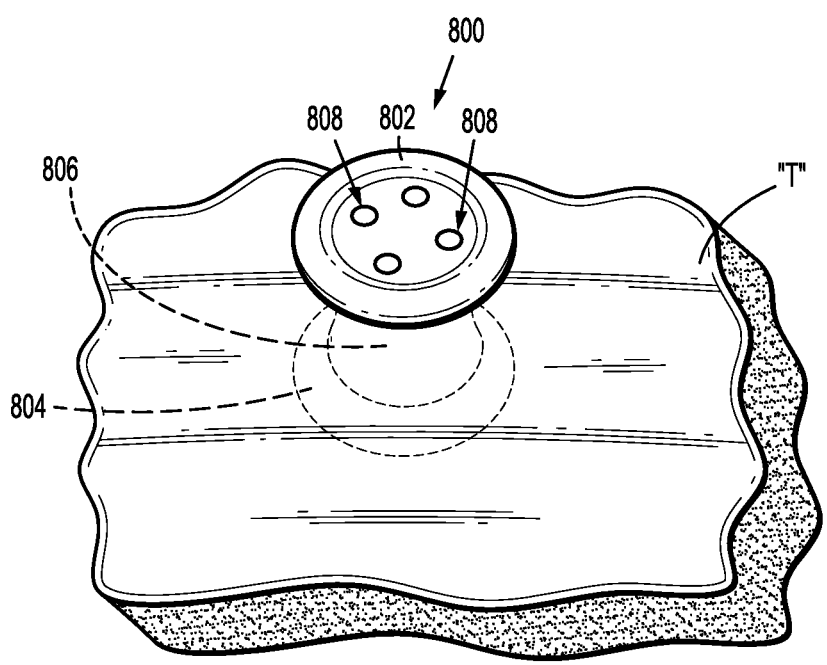
FIG. 14B is top, perspective view of the surgical access port of FIG. 14A inserted into an incision in tissue.

Turning now to FIGS. 14A-14B, another embodiment of an access port, or seal anchor member 800 is shown. Seal anchor member 800, along with other embodiments of access ports that may be used in conjunction with surgical access system 10, are disclosed in commonly-owned, co-pending U.S. patent application Ser. No. 12/244,024 to Richard et al., filed Oct. 2, 2008, the entire contents of which are hereby incorporated by reference herein. Accordingly, seal anchor member 800 will only be summarily described herein.

Seal anchor member 800 includes respective proximal and distal rims 802, 804 and an intermediate portion 806 extending longitudinally between the proximal and distal rims 802, 804, respectively. Seal anchor member 800 further includes one or more ports 808 that extend longitudinally between proximal and distal rims 802, 804, respectively, and through seal anchor member 800.

Seal anchor member 800 is formed of a biocompatible compressible material that facilitates the resilient, reciprocal transitioning of seal anchor member 800 between an expanded condition (FIG. 14B) and a compressed condition (FIG. 14A). Seal anchor member 800 is preferably formed from a suitable foam material having sufficient compliance to form a seal about one or more surgical objects inserted through one or more of ports 808 and to establish a sealing relation with tissue "T." The foam is preferably sufficiently compliant to accommodate off axis motion of the surgical object when inserted therethrough. In one embodiment, the foam includes a polyisoprene material. The foam may also be a "memory" foam such that seal anchor member 800 is resiliently transitionable between the expanded condition (FIG. 14B) and the compressed condition (FIG. 14A).

With continued reference to FIGS. 14A-14B, proximal and distal rims 802, 804, respectively, of seal anchor member 800 extend radially outwardly from seal anchor member 800, while intermediate portion 806 defines a reduced diameter such that seal anchor member 800 defines an "hour-glass" shape or configuration to assist in anchoring seal anchor member 800 within tissue. However, other configurations of seal anchor member 800 are also contemplated.

Each port 808 of seal anchor member 800 is configured to removably receive one or more surgical objects therethrough in sealing relation therewith. Prior to the insertion of a surgical object, ports 808 are disposed in a first state wherein each port 808 defines a closed configuration such that the escape of insufflation gas (not shown) through ports 808 of seal anchor member 800 is substantially inhibited. Upon the introduction of a surgical object, the port 808 transitions to a second state wherein port 808 expands in diameter to substantially approximate the diameter of the surgical object, creating a seal therearound.

As mentioned above, seal anchor member 800 is adapted to transition from an expanded condition (FIG. 14B) to a compressed condition (FIG. 14A) so as to facilitate the insertion and securement thereof within an incision in tissue "T." More particularly, once an incision has been formed through body tissue "T," seal anchor member 800 is squeezed or compressed to reduce seal anchor member 800 from the expanded condition to the compressed condition, as shown in FIG. 14A. Seal anchor member 800 may be compressed into any suitable configuration prior to being inserted into an incision, not merely the configuration shown in FIG. 14A.

Referring now to FIG. 14B, once seal anchor member 800 has been inserted through the incision in tissue "T," the pressure, e.g., the squeezing or compression force, applied to seal anchor member 800 is released, allowing seal anchor member 800 to return towards the expanded, or uncompressed condition. Typically, the incision is formed having a size that is slightly smaller than the diameter of the seal anchor member 800 in the expanded state such that, once places within the incision in tissue "T," seal anchor member 800 is sealing engaged therein. Once positioned as described above, one or more surgical objects, e.g., surgical access system 10 (FIG. 1), may be inserted through ports 808 to perform a surgical task within the internal surgical site.

Referring now to FIGS. 15A-15B, another embodiment of an access port, or seal anchor member 900 is disclosed. Seal anchor member 900 is similar to seal anchor member 800 (FIGS. 14A-14B) and, accordingly, similar features will be summarized hereinbelow while the differences thereof will be described in greater detail. Seal anchor member 900, similar to seal anchor member 800 includes respective proximal and distal ends 902, 904, an intermediate portion 906 disposed between the proximal and distal ends 902, 904, and one or more generally tubular port segments 908 defining ports 909 that extend longitudinally through seal anchor member 900 and between the proximal and distal ends 902, 904. Proximal and distal ends 902, 904 each define a rim 910, 912, respectively, of seal anchor member 900 that facilitates the anchoring of seal anchor member 900 within tissue "T."

With continued reference to FIGS. 15A-15B, tubular port segments 908 are secured to seal anchor member 900 by a plurality of connective members 914 such that the longitudinal position of the port segments 908 remain substantially constant with respect to the respective proximal and distal rims 910, 912 during insertion and removal of a surgical object therefrom. As shown, each of the connective members 914 extends inwardly from the seal anchor member 900 and is attached to one of the ports 908. Further, several interconnective members 916 are disposed between the port segments 908 to interconnect the port segments 908 to one another. Connective members 914 (and/or the interconnective members 916) may be composed of the same material comprising seal anchor member 900 or, alternatively, may be composed of a material that is substantially more rigid, to inhibit off-axis movement of the surgical object "O" following its insertion into one of the ports 908, or substantially less rigid, to facilitate off-axis movement of the surgical object "O."

Continuing with reference to FIGS. 15A-15B, ports 908 extend longitudinally through seal anchor member 900 such that the proximal ends 918 of the ports 908 are substantially coplanar with the proximal rim 910 of seal anchor member 900 and such that the distal ends 920 of the ports 908 are substantially coplanar with the distal rim 912 of seal anchor member 900. However, it is also envisioned that the proximal and distal ends 918, 920 of ports 908 extend beyond the proximal and distal rims 902, 904, or that the proximal and distal ends 916, 918 of ports 908 are defined entirely within the intermediate portion 906 thereof. The insertion and operation of seal anchor member 900 is similar to that of seal anchor member 800 (see FIGS. 14A-14B), discussed above, and, thus, will not be repeated here.

Referring now to FIG. 16, the use and operation of surgical access system 10, as described in detail with reference to the various embodiments thereof, will be summarized in order to interrelate and provide appreciation for the various components and features of surgical access system 10. In FIG. 16, surgical access system 10 is shown including a pair of cannula arms 100 each having an articulation assembly 400 coupled thereto and a gimbal assembly 500 disposed at a proximal end thereof.

Initially, an access port 1000 (or any other suitable access port, such as those described above) is positioned within an incision in tissue "T" or a naturally occurring orifice (e.g., anus or vagina). Thereafter, cannula arms 100 are each inserted distally through the access portion 1000 in the substantially straight configuration such that the distal ends 109 thereof are positioned adjacent the internal surgical site. Prior or subsequent to insertion, cannula arms 100 may be secured to one another via retaining clip 600, as described above. Next, a surgical instrument "I1," "I2" is inserted through each of the cannula arms 100 such that the end effector assemblies 24a, 24b, respectively, thereof extend distally from cannula arms 100 and such that the handle assemblies 20a, 20b, respectively, thereof extend proximally from gimbal assemblies 500. With surgical instruments "I1" and "I2" in position within surgical access device 10, the proximal portions of cannula arms 100 may be selectively manipulated such that articulation mechanism 400 translates motion thereof to articulate first articulatable segments 120 of cannula arm 100 to a desired position and/or handle assemblies 20a, 20b may be selectively manipulated to swivel the corresponding gimbal assemblies 500 such that second articulatable segments 140 are articulated to a desired configuration. As can be appreciated, the independent articulation of each of the cannula arms 100 and of the first and second articulatable segments 120, 140, respectively, thereof facilitates positioning of end effector assemblies 24a, 24b in various different positions relative to one another to perform a surgical task within the internal surgical site. For example, as shown in FIG. 16, both cannula arms 100 are disposed in the fourth configuration (see FIG. 2D), defining opposed C-shaped configurations such that end effector assemblies 24a, 24b extend toward one another. This configuration is advantageous in that the effector assemblies 24a, 24b are opposed, i.e., facing, one another, rather than adjacent to, i.e., side-by-side, one another, thus facilitating performing a surgical task within the internal surgical site that requires cooperation of instruments "I1" and "I2."

FIG. 16 shows one embodiment of surgical access system 10 wherein an articulation mechanism 400 is coupled to each of the cannula arms 100 for selectively articulating first articulatable segments 120 of cannula arms 100. However, it is envisioned that any of the other articulation mechanisms, e.g., articulation mechanisms 200 and 300, may be used in conjunction with either or both of the cannula arms 100 as part of surgical access system 10. The use of surgical access system 10 in conjunction with these embodiments, i.e., with articulation mechanisms 200 or 300, is substantially similar to that as described above with reference to FIG. 16, except for the specific operation of the particular articulation mechanism 200, 300 (which are described in detail above with reference to FIGS. 10A-10B and 11A-11B, respectively), and, thus, will not be repeated herein for purposes of brevity.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical system, comprising:
   at least one arm defining a longitudinal passageway extending therethrough configured to receive a surgical instrument therein, the at least one arm including a proximal portion configured for positioning externally of a patient's body and a distal portion configured for positioning within an internal body cavity, the distal portion including first and second articulatable segments spaced-apart from one another and capable of independent articulation between a substantially straight configuration and an articulated configuration;
   a first articulation assembly coupled to the proximal portion of the at least one arm, the first articulation assembly transitionable between a first state and a second state for articulating the first articulatable segment between the substantially straight configuration and the articulated configuration, the first articulation assembly including a lever and a base, the first articulatable segment articulating between the substantially straight configuration and the articulated configuration in response to the lever moving relative to the base between a spaced-apart position and an approximated position; and
   a second articulation assembly coupled to the proximal portion of the at least one arm, the second articulation assembly different from the first articulation assembly, the second articulation assembly configured to move between a plurality of positions for articulating the second articulatable segment between the substantially straight configuration and the articulated configuration.

2. The surgical system according to claim 1, wherein at least one set of articulation cables extends from each of the first and second articulatable segments to the first and second articulation assemblies, respectively, each set of articulation cables selectively tensionable for articulating one of the first and second articulatable segments.

3. The surgical system according to claim 1, further comprising a locking assembly configured to fix the lever in position relative to the base to fix the position of the first articulatable segment.

4. The surgical system according to claim 1, wherein the locking assembly is automatically engaged to lock the lever in position when the lever is moved to the approximated position such that the first articulatable segment is locked in the articulated position.

5. A surgical system, comprising:
   at least one arm defining a longitudinal passageway extending therethrough configured to receive a surgical instrument therein, the at least one arm including a proximal portion configured for positioning externally of a patient's body and a distal portion configured for positioning within an internal body cavity, the distal portion including first and second articulatable segments spaced-apart from one another and capable of independent articulation between a substantially straight configuration and an articulated configuration;
   a first articulation assembly coupled to the proximal portion of the at least one arm, the first articulation assembly transitionable between a first state and a second state for articulating the first articulatable segment between the substantially straight configuration and the articulated configuration, wherein the first articulation assembly includes first and second components pivotable relative to one another between a substantially aligned position and a substantially transverse position for articulating the first articulatable segment between the substantially straight configuration and the articulated configuration; and
   a second articulation assembly coupled to the proximal portion of the at least one arm, the second articulation assembly different from the first articulation assembly, the second articulation assembly configured to move between a plurality of positions for articulating the second articulatable segment between the substantially straight configuration and the articulated configuration.

6. The surgical system according to claim 5, further comprising a locking assembly, the locking assembly configured to fix the first and second components in position relative to one another upon pivotable movement of the first and second components to at least one pre-determined position relative to one another.

7. The surgical system according to claim 6, wherein the locking assembly includes a slide block, the slide block selectively translatable to release the first and second components from fixed positions relative to one another.

8. The surgical system according to claim 1, further comprising an access portal configured for positioning within an incision in tissue, the access portal configured to receive the at least one arm therethrough for positioning of the distal portion of the at least one arm within the internal body cavity.

9. A surgical system, comprising:
   at least one arm defining a longitudinal passageway extending therethrough configured to receive a surgical instrument therein, the at least one arm including a proximal portion configured for positioning externally of a patient's body and a distal portion configured for positioning within an internal body cavity, the distal portion including first and second articulatable segments spaced-apart from one another and capable of independent articulation between a substantially straight configuration and an articulated configuration;
   a first articulation assembly coupled to the proximal portion of the at least one arm, the first articulation assembly transitionable between a first state and a second state for articulating the first articulatable segment between the substantially straight configuration and the articulated configuration; and
   a second articulation assembly coupled to the proximal portion of the at least one arm, the second articulation assembly different from the first articulation assembly, the second articulation assembly configured to move between a plurality of positions for articulating the second articulatable segment between the substantially straight configuration and the articulated configuration, wherein the second articulation assembly includes:
   a base defining a cavity; and
   a rotatable member movably disposed in the cavity of the base and movable relative to the base to articulate the second articulatable segment between the substantially straight and articulated configurations, the rotatable member transitionable between an unlocked state, wherein the rotatable member is movable within the cavity of the base relative to the base, and a locked state, wherein an orientation of the rotatable member is fixed relative to the base.

10. The surgical system according to claim 9, wherein the rotatable member includes a port extending therethrough in communication with the longitudinal passageway of the at least one arm, the port configured to receive the surgical instrument therein.

11. The surgical system according to claim 10, wherein movement of the surgical instrument disposed within the port of the rotatable member relative to the base articulates the second articulatable segment between the substantially straight and articulated configurations.

12. The surgical system according to claim 5, wherein at least one set of articulation cables extends from each of the first and second articulatable segments to the first and second articulation assemblies, respectively, each set of articulation cables selectively tensionable for articulating one of the first and second articulatable segments.

13. The surgical system according to claim 5, further comprising an access portal configured for positioning within an incision in tissue, the access portal configured to receive the at least one arm therethrough for positioning of the distal portion of the at least one arm within the internal body cavity.

14. The surgical system according to claim 9, wherein at least one set of articulation cables extends from each of the first and second articulatable segments to the first and second articulation assemblies, respectively, each set of articulation cables selectively tensionable for articulating one of the first and second articulatable segments.

15. The surgical system according to claim 9, further comprising an access portal configured for positioning within an incision in tissue, the access portal configured to receive the at least one arm therethrough for positioning of the distal portion of the at least one arm within the internal body cavity.

* * * * *